US011116782B2

(12) United States Patent
Zeldis

(10) Patent No.: US 11,116,782 B2
(45) Date of Patent: Sep. 14, 2021

(54) METHODS OF TREATING MYELODYSPLASTIC SYNDROMES WITH A COMBINATION THERAPY USING LENALIDOMIDE AND AZACITIDINE

(71) Applicant: Celgene Corporation, Summit, NJ (US)

(72) Inventor: Jerome B. Zeldis, Princeton, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 16/419,780

(22) Filed: May 22, 2019

(65) Prior Publication Data

US 2019/0269712 A1 Sep. 5, 2019

Related U.S. Application Data

(60) Continuation of application No. 15/926,740, filed on Mar. 20, 2018, now abandoned, which is a continuation of application No. 14/517,280, filed on Oct. 17, 2014, now Pat. No. 9,925,207, which is a continuation of application No. 13/801,262, filed on Mar. 13, 2013, now Pat. No. 9,056,120, which is a continuation of application No. 12/777,765, filed on May 11, 2010, now Pat. No. 8,404,716, which is a continuation-in-part of application No. 11/985,032, filed on Nov. 12, 2007, now Pat. No. 7,863,297, which is a continuation of application No. 11/654,550, filed on Jan. 16, 2007, now Pat. No. 7,393,863, which is a division of application No. 10/411,649, filed on Apr. 11, 2003, now Pat. No. 7,189,740.

(60) Provisional application No. 60/418,468, filed on Oct. 15, 2002.

(51) Int. Cl.
| A61K 31/706 | (2006.01) |
| A61K 31/454 | (2006.01) |
| A61K 45/06 | (2006.01) |
| A61K 39/395 | (2006.01) |
| A61P 35/02 | (2006.01) |

(52) U.S. Cl.
CPC .......... *A61K 31/706* (2013.01); *A61K 31/454* (2013.01); *A61K 39/3955* (2013.01); *A61K 45/06* (2013.01); *A61P 35/02* (2018.01)

(58) Field of Classification Search
CPC ............................. A61K 31/454; A61K 31/706
See application file for complete search history.

(56) References Cited

U.S. PATENT DOCUMENTS

| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,551,177 A | 11/1985 | Trubiano et al. |
| 4,810,643 A | 3/1989 | Souza |
| 4,999,291 A | 3/1991 | Souza |
| 5,059,595 A | 10/1991 | LeGrazie |
| 5,073,543 A | 12/1991 | Marshall et al. |
| 5,120,548 A | 6/1992 | McClelland et al. |
| 5,134,127 A | 7/1992 | Stella et al. |
| 5,229,496 A | 7/1993 | Deeley et al. |
| 5,288,487 A | 2/1994 | Kawashima et al. |
| 5,354,556 A | 10/1994 | Sparks et al. |
| 5,385,901 A | 1/1995 | Kaplan et al. |
| 5,391,485 A | 2/1995 | Deeley et al. |
| 5,393,870 A | 2/1995 | Deeley et al. |
| 5,528,823 A | 6/1996 | Rudy et al. |
| 5,580,755 A | 12/1996 | Souza |
| 5,591,767 A | 1/1997 | Mohr et al. |
| 5,593,696 A | 1/1997 | McNally et al. |
| 5,593,990 A | 1/1997 | D'Amato |
| 5,594,637 A | 1/1997 | Eisenberg et al. |
| 5,619,991 A | 4/1997 | Sloane |
| 5,629,327 A | 5/1997 | D'Amato |
| 5,635,517 A * | 6/1997 | Muller .................. A61K 9/107 514/323 |
| 5,639,476 A | 6/1997 | Oshlack et al. |
| 5,641,758 A | 6/1997 | Kluge et al. |
| 5,643,915 A | 7/1997 | Andrulis et al. |
| 5,674,533 A | 10/1997 | Santus et al. |
| 5,698,579 A | 12/1997 | Muller |
| 5,712,291 A | 1/1998 | D'Amato |
| 5,731,325 A | 3/1998 | Andmlis, Jr. et al. |

(Continued)

FOREIGN PATENT DOCUMENTS

| JP | 11-286455 | 10/1999 |
| JP | 2002-513391 | 5/2002 |

(Continued)

OTHER PUBLICATIONS

Lewis R. Silverman et al. Effects of Treatment with 5-Azacytidine on the In vivo and In vitro Hematopoiesis in Patients with Myelodysplastic Syndromes, Leukemia, vol. 7, Suppl. Monograph 1, 21-29. (Year: 1993).*

Francesca Zorat et al. The Clinical and biological effects of thalidomide in patients with myelodysplastic syndromes, British J. Haematology, 115, 881-894. (Year: 2001).*

Zorat et al. The Clinical and biological effects of thalidomide in patients with myelodysplastic syndromes, British J Haematology, 115, 881-894. (Year: 2001).*

Silverman et al. Leukemia vol. 7, 21-29. (Year: 1993).*

(Continued)

*Primary Examiner* — Michael G. Hartley
*Assistant Examiner* — Jagadishwar R Samala
(74) *Attorney, Agent, or Firm* — Jones Day

(57) ABSTRACT

Methods of treating, preventing and/or managing myelodysplastic syndromes are disclosed. Specific methods encompass the administrations of 3-(4-amino-1-oxo-1,3-dihydroisoindol-2-yl)-piperidin-2,6-dione in combination with 5-azacytidine.

11 Claims, No Drawings

(56) References Cited

U.S. PATENT DOCUMENTS

| | | |
|---|---|---|
| 5,733,566 A | 3/1998 | Lewis |
| 5,798,368 A | 8/1998 | Muller et al. |
| 5,832,449 A | 11/1998 | Cunningham |
| 5,874,448 A | 2/1999 | Muller et al. |
| 5,877,200 A | 3/1999 | Muller |
| 5,882,656 A | 3/1999 | Bechard et al. |
| 5,929,117 A | 7/1999 | Muller et al. |
| 5,955,476 A | 9/1999 | Muller et al. |
| 5,974,203 A | 10/1999 | Tadokoro et al. |
| 6,011,050 A | 1/2000 | Muller et al. |
| 6,045,501 A | 4/2000 | Elsayed et al. |
| 6,055,507 A | 4/2000 | Cunningham |
| 6,063,026 A | 5/2000 | Schauss et al. |
| 6,071,948 A | 6/2000 | D'Amato |
| 6,096,757 A | 8/2000 | Bishop et al. |
| 6,131,090 A | 10/2000 | Basso et al. |
| 6,202,923 B1 | 3/2001 | Boyer et al. |
| 6,228,879 B1 | 5/2001 | Green et al. |
| 6,281,230 B1 | 8/2001 | Muller et al. |
| 6,315,720 B1 | 11/2001 | Williams et al. |
| 6,316,471 B1 | 11/2001 | Muller et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,420,414 B1 | 7/2002 | D'Amato |
| 6,432,924 B1 | 8/2002 | Nyce |
| 6,458,810 B1 | 10/2002 | Muller et al. |
| 6,469,045 B1 | 10/2002 | D'Amato |
| 6,476,052 B1 | 11/2002 | Muller et al. |
| 6,518,298 B2 | 2/2003 | Green et al. |
| 6,555,554 B2 | 4/2003 | Muller et al. |
| 6,561,976 B2 | 5/2003 | Elsayed et al. |
| 6,561,977 B2 | 5/2003 | Williams et al. |
| 6,673,828 B1 | 1/2004 | Green et al. |
| 6,755,784 B2 | 6/2004 | Williams et al. |
| 6,878,733 B1 | 4/2005 | Shenoy et al. |
| 6,887,855 B2 | 5/2005 | Ionescu et al. |
| 6,890,547 B1 | 5/2005 | Takada et al. |
| 6,896,399 B2 | 5/2005 | Nomura et al. |
| 6,908,432 B2 | 6/2005 | Elsayed et al. |
| 6,943,249 B2 | 9/2005 | Ionescu et al. |
| 7,078,518 B2 | 7/2006 | Ionescu et al. |
| 7,119,106 B2 | 10/2006 | Muller et al. |
| 7,189,740 B2 | 3/2007 | Zeldis |
| 7,393,862 B2 | 7/2008 | Zeldis |
| 7,393,863 B2 | 7/2008 | Zeldis |
| 7,465,800 B2 | 12/2008 | Jaworsky et al. |
| 7,855,217 B2 | 12/2010 | Jaworski et al. |
| 7,959,566 B2 | 6/2011 | Williams et al. |
| 7,968,569 B2 | 6/2011 | Zeldis |
| 8,158,653 B2 | 4/2012 | Muller et al. |
| 8,188,118 B2 | 5/2012 | Zeldis |
| 8,198,262 B2 | 6/2012 | Zeldis |
| 8,198,306 B2 | 6/2012 | Zeldis |
| 8,204,763 B2 | 6/2012 | Elsayed et al. |
| 8,207,200 B2 | 6/2012 | Zeldis |
| 8,315,886 B2 | 11/2012 | Williams et al. |
| 8,530,498 B1 | 9/2013 | Zeldis |
| 8,589,188 B2 | 11/2013 | Elsayed et al. |
| 8,626,531 B2 | 1/2014 | Williams et al. |
| 8,648,095 B2 | 2/2014 | Zeldis |
| 8,673,939 B2 | 3/2014 | Zeldis |
| 8,735,428 B2 | 5/2014 | Zeldis |
| 8,828,427 B2 | 9/2014 | Tutino et al. |
| 9,101,621 B2 | 8/2015 | Zeldis |
| 9,101,622 B2 | 8/2015 | Zeldis |
| 2001/0021380 A1 | 9/2001 | Pluenneke |
| 2001/0026807 A1 | 10/2001 | Watts |
| 2001/0056114 A1 | 12/2001 | D'Amato |
| 2002/0035090 A1 | 3/2002 | Zeldis et al. |
| 2002/0045643 A1 | 4/2002 | Muller et al. |
| 2002/0051820 A1 | 5/2002 | Shell et al. |
| 2002/0052398 A1 | 5/2002 | D'Amato |
| 2002/0054899 A1 | 5/2002 | Zeldis et al. |
| 2002/0061923 A1 | 5/2002 | D'Amato |
| 2002/0161023 A1 | 10/2002 | D'Amato |
| 2002/0173658 A1 | 11/2002 | Muller et al. |
| 2002/0183360 A1 | 12/2002 | Muller et al. |
| 2003/0028028 A1 | 2/2003 | Man et al. |
| 2003/0039688 A1 | 2/2003 | Shell et al. |
| 2003/0045552 A1 | 3/2003 | Robarge et al. |
| 2003/0049311 A1 | 3/2003 | McAllister et al. |
| 2003/0069428 A1 | 4/2003 | Muller et al. |
| 2003/0096841 A1 | 5/2003 | Robarge et al. |
| 2003/0104053 A1 | 6/2003 | Gusler et al. |
| 2003/0104062 A1 | 6/2003 | Berner et al. |
| 2003/0139451 A1 | 7/2003 | Shah et al. |
| 2003/0144325 A1 | 7/2003 | Muller et al. |
| 2003/0181428 A1 | 9/2003 | Green et al. |
| 2003/0187024 A1 | 10/2003 | D'Amato |
| 2003/0191098 A1 | 10/2003 | D'Amato |
| 2003/0220254 A1 | 11/2003 | Khan et al. |
| 2003/0235909 A1 | 12/2003 | Hariri et al. |
| 2004/0029832 A1 | 2/2004 | Zeldis |
| 2004/0077685 A1 | 4/2004 | Figg et al. |
| 2004/0077686 A1 | 4/2004 | Dannenberg et al. |
| 2004/0087546 A1 | 5/2004 | Zeldis |
| 2004/0091455 A1 | 5/2004 | Zeldis |
| 2004/0122052 A1 | 6/2004 | Muller et al. |
| 2004/0152632 A1 | 8/2004 | Feingold |
| 2004/0162263 A1 | 8/2004 | Sands et al. |
| 2005/0272675 A1 | 12/2005 | Ionescu et al. |
| 2006/0247189 A1 | 11/2006 | Ionescu et al. |
| 2007/0155791 A1 | 7/2007 | Zeldis et al. |
| 2007/0270374 A1 | 11/2007 | Gallop |
| 2008/0057086 A1 | 3/2008 | Etter |
| 2009/0286752 A1 | 11/2009 | Etter et al. |
| 2010/0278779 A1 | 11/2010 | Zeldis |
| 2011/0172273 A1 | 7/2011 | Zeldis |

FOREIGN PATENT DOCUMENTS

| | | |
|---|---|---|
| WO | WO 92/06712 | 4/1992 |
| WO | WO 92/14455 | 9/1992 |
| WO | WO 94/20085 | 9/1994 |
| WO | WO 96/13790 | 5/1996 |
| WO | WO 98/03502 | 1/1998 |
| WO | WO 98/13783 | 4/1998 |
| WO | WO 98/19649 | 5/1998 |
| WO | WO 98/54170 | 12/1998 |
| WO | WO 99/10829 | 3/1999 |
| WO | WO 00/51053 | 8/2000 |
| WO | WO 01/70275 | 9/2001 |
| WO | WO 01/87306 | 11/2001 |
| WO | WO 01/87307 | 11/2001 |
| WO | WO 2002/015926 | 2/2002 |
| WO | WO 02/059106 | 8/2002 |
| WO | WO 02/064083 | 8/2002 |
| WO | WO 03/086373 | 10/2003 |
| WO | WO 03/097040 | 11/2003 |
| WO | WO 03/097052 | 11/2003 |
| WO | WO 04/035064 | 4/2004 |
| WO | WO 05/110085 | 11/2005 |
| WO | WO 05/110408 | 11/2005 |
| WO | WO 2006/063111 | 6/2006 |
| WO | WO 2008/027049 | 3/2008 |
| WO | WO 2008/028193 | 3/2008 |
| WO | WO 2009/052287 | 4/2009 |
| WO | WO 2009/058394 | 5/2009 |

OTHER PUBLICATIONS

"CDC Meeting: Mar. 26, 1997 Minutes and Agenda Regarding Thalidomide" ("CDC Meeting").

"Celgene's Revlimid an orphan drug, says FDA," Marketletter Oct. 15, 2001.

Center for Drug Evaluation and Research Approval Package for Application No. 18-662/S-038 ("Accutane Label").

"Center for drug evaluation and research approval package for: Application No. NDA 20-785 approval letter(s)," Sep. 19, 1997 and Jul. 16, 1998.

(56) References Cited

OTHER PUBLICATIONS

"Center for Drug Evaluation and Research Approval Package for: Application No. NDA 20-785 Approval Letter(s)," Sep. 19, 1997, and Jul. 16, 1998 ("FDA Thalomid Approval Letters").
"Center for drug evaluation and research approval package for: Application No. 18-662/S-038."
Thalomid™ (thalidomide) Capsules Revised Package Insert (Jul. 15, 1998) ("'Thalomid PT'") published on or about Jul. 15, 1998. "The restricted program is called System for Thalidomide Education and Prescribing Safety, (i.e., S.T.E.P.S.)."
"EntreMed moves towards commercialization with production of thalidomide analogs; Next generation drug candidates to be manufactured in preparation for clinical studies," PR Newswire Aug. 7, 2001.
A National, Open-Label, Multicenter, Randomized, Phase III Study of Revlimid (Lenalidomide) and Dexamethasone (ReDex) Treatment Versus Observation in Patients With Smoldering Multiple Myeloma With High Risk of Progression (NCT00480363 on Nov. 26, 2008 at ClirocalTrials.gov).
Adams et al., "Proteasome inhibitors: A novel class of potent and effective antitumor agents," Cancer Res. 59:2615-2622 (1999).
Alder et al., "The Return of Thaliomide—A shunned compound makes a scientific comeback," Science News 146: 424-425 (1994).
Alexanian et al., "High-dose glucocorticoid treatment of resistant myeloma," Ann. Intern. Med. 105:8-11 (1986).
Alexanian et al., "Consolidation therapy of multiple myeloma with thalidomide-dexamethasone after intensive chemotherapy," Ann Oncol. 13:1116-9 (2002).
Alvi, S., Anthwal, S., Shaikh, M., Shatter, A., Shetty, V., Mundle, S., Reddy P., Allampallam, K., Bi, S., Zorat, F., Tamosveiciene, D., Rasila, K., Meagher, R., Westbrook, C., Galili, N., Gezer, S., Venugopal, P., Borok, R.Z., Raza, A., Thalidomide significantly augments proliferation and cytokine secretion to bone marrow cultures established from myelodysplastic syndrome (MDS) patients. Abstract #1484, American Society of Hematology, Dec. 7-11, 2001.
Alvi, S., Henderson, B., Shaher, A., Dangerfield, B., Broderick, E., Jafri, N., Tareen, M., Durandt, M., Galili, N., Borok, R.Z., Raza, A., Determination of clonality in stromal and parenchymal cells pre and post thalidomide treatment in myelodysplasia. Abstract #1536, American Society of Hematology, Dec. 1-5, 2000.
Alvi, S., Shakier, A., Henderson, B., Dar, S., Zorat, F., Broderick E, Lisak, L., Durandt, M., Reddy, P., Mundle, S., Galili, N, Borok, R.Z., Raza, A., Improved growth of stromal cells in long term bone marrow cultures (LTBMC) of myelodysplastic syndrome (MDS) patients treated with thalidomide. Abstract #1547, American Society of Hematology, Dec. 1-5, 2000.
Alvi, S., Shaher, A., Shaikh, M., Anthwal, S., Siddiqi, F., Akhtar, a., Ashraf, H., Meager, R., Mundle, S., Shetty, V., Goldberg, C., Galili, N., Borok, R.Z., Raza, A., MDS patients with hematological response to thalidomide show enhanced in vitro growth potential. Abstract #1482, American Society.
Alvi, S., Shaikh, M., Anthwal, S., Shaher, A., Tamoseviciene, D., Novick, A., Reddy, P., Allampallam, K., Hsu, W.T., Galili, N., Borok, R.Z., Raza, A., Cytogenetic and clonal profile of myelodysplastic syndromes (MDS) patients treated with thalidomide. Abstract #1483, American Society of Hematology, Dec. 7-11, 2001.
Anders, O., Plath, F., Emmrich, J., Freund, M., Complete remission of therapy-resistant angiodysplasia of the stomach in myelodysplastic syndrome following thalidomide. Abstract #3820, American Society of Hematology, Dec. 7-11, 2001.
Anderson et al., "Multiple myeloma: New insights and therapeutic approaches," Hematology Am. Soc. Hematol. Educ. Program 2000:147-165 (2000).
Aparicio et al., Current Opinion in Investigational Drugs, 2002, 3(4), 627-33.
Argemi et al., Journal of Pharmaceutical and Biomedical Analysis, 2007, 44, 859-66.
Bain, Barbara J., "The Relationship between the Myelodysplastic Syndromes and the Myeloproliferative Disorders," Leukemia & Lymphoma, 1999, 34(5-6):443-449.
Baker, AF; Bellamy, WT; Glinsmann-Gibson, B; Heaton, R.; Buresh, A.; Grogan, TM; List, AF; "Biological response to Thalidomide in Remitting Patients with Myelodysplastic Syndrome (MDS) Evidence for Induction of Neoplastic Vascular Endothelial Growth Factor (VEGF) Resistance" Blood 2001; 98(11):353a-4a, Abstract #1490.
Balaian et al., "5-Azacylidine Augments the Cytotoxicity of Mylotarg Toward AML Blasts In Vitro and In Vivo," Blood, 2007, 110(11), Part 1, 543A-544A (American Society of Hematology, Annual Meeting, Dec. 8-11, 2007, Abstract #1835).
Barlogie et al., "Effective Treatment of Advanced Multiple Myeloma Refractory to Alkylating Agents," N. Engl. J. Med.310(21):1353-1356 (1984).
Barlogie, B., Desikan, R., Munshi, N., Siegel, D., Mehta, J., Singhal, S., Anaissie, E., Single Course D.T. Pace Anti-Angiochemotherapy Effects CR in Plasma Cell Leukemia and Fulminant Multiple Myeloma (MM). Abstract #4180. American Society of Hematology, Dec. 4-9, 1998.
Beazley et al., 1985, "Malignant structure at the confluence of the biliary tree: diagnosis and management," Surg. Annu., 1985, 17:125-41.
Beisler et al., Journal of Medicinal Chemistry, 1977, 20(6), 806-12.
Bellamy et al., 2001, "Vascular endothelial cell growth factor is an autocrine promoter of abnormal localized immature myeloid precursors and leukemia progenitor formation in myelodysplastic syndromes," Blood 97:1427-1434.
Bellet et al., Cancer Chemotherapy Reports, Part I, 1974, 58(2), 217-22.
Bellet et al., Medical and Pediatric Oncology, 1978, 4, 11-15.
Bennett et al., 1982, "Proposals for the classification of the myelodysplastic syndromes," Br. J. Haematol. 51:189-199.
Bennett et al., 1985, "Proposed revised criteria for the classification of acute myeloid leukemia. A report of the French-American-British Cooperative Group," Ann. Intern. Med. 103(4):620-625.
Besa et al., 1990, 76(Supp. 1):133a.
Besa, 1992, "Myelodysplastic syndromes (refractory anemia). A perspective of the biologic, clinical, and therapeutic issues," Med. Clin. North Am. 76(3):599-617.
Bhuyan et al., Cancer Research, 1972, 32, 398-407.
Bhuyan et al., Cancer Research, 1973, 33, 888-94.
Bjorkstrand et al., "Prognostic factors in autologous stem cell transplantation for multiple myeloma: an EBMT registry study," Leuk. Lymphoma, 15(3-4):265-272 (1994).
Bor, "Thalidomide shows that it can heal, too from deformer of babies to force for good," Baltimore Sun Apr. 2, 1995.
Bor, J., Thalidomide shows that it can heal, too from deformer of babies to force for good, Baltimore Sun, Apr. 2, 1995 ("Bor") http://articles.baltimoresun.com/1995-04-02/news/1995092001_1_thalidomide-birth-defects-deformities.
Bours, V; Franzoso, G; Brown, K.; Park, S.; Azarenko, V.; Tomita-Yamaguchi, M ; Kelly, K.; Siebenilist, U.; "Lymphocyte Activiation and the Family of NF-kB Transcription Facor Complexes." Corrent Topics in Microbiology and Immunology 1992; 182: 411-20.
Bowen et al., 1991, "The treatment of anaemia in the myelodysplastic syndromes with recombinant human erythropoietin," Br. J. Haematol, 77(3):419-423.
Braulke et al., "FISH-Analyses of Circulating CD34+ Cells in MDS Patients—A Suitable Method to Measure and Predict Response to 5-Azacytidine," Blood, 2007, 110(11), Part 1, 727A-728A (American Society of Hematology, Annual Meeting, Dec. 8-11, 2007, Abstract #2466).
Breistol, K. et al., "Antitumor Activity of P-4055 (elaidic acid-cytarabine) Compared to Cytarbine in Metastatic and s.c. Human Tumor Xenograft Models," Cancer Research, 1999, 59(12):2944-2949.
Brock et al., New England Journal of Medicine, 2008, 358(11), 1118-28.
Broder et al., "Dideoxycytidine: current clinical experience and future prospects. A summary," Am. J. Med., 88(5B):31S-33S (1990).
Bunn et al., 2003, "Emergences of clonal cytogenic abnormalities in pH- cells in some CML patients in cytogenic remission to imatinib but restoration of polyclonal hematopoiesis in the majority." Blood. 101:1941-1949.

(56) References Cited

OTHER PUBLICATIONS

Burleson, K.W., "Review of computer applications in institutional pharmacy—1975-1981," Am. J. Hosp. Pharm. 39(1): 53-70 (1982).
Bwire et al., Managing the Teratogenic Risk of Thalidomide and Lenalidomide: An Industry Perspective, Expert Opin. Drug Saf., 10(1):3-8 (2011).
Cairo, "Dose reductions and delays: Limitations of myelosuppressive chemotherapy," Cancer Network Sep. 1, 2000.
Canal et al., "Benefits of pharmacological knowledge in the design and monitoring of cancer chemotherapy," Pathology Oncol. Res., 4(3):171-178 (1998).
Cancer Therapy Evaluation Program, 1998, "Common toxicity criteria," Version 2.0, Bethesda, MD: Division of Cancer Treatment and Diagnosis, National Institutes of Health, Mar. 1998. (Accessed Jan. 18, 2005, at http://ctep.cancer.gov/reporting/ctc.html.).
Cartensen, 1995, Drug Stability: Principles & Practice, 2nd ed., Marcel Dekker, New York, NY pp. 379-380.
Celgene Corporation Awarded Additional Patent Protection for Lead IMiD(TM), REVIMED(TM); Comprehensive Patent Protection for REVIMID Includes Coverage of the Active Ingredient, Pharmaceutical Compositions, and Therapeutic Uses PR Newswire; Aug. 28, 2001.
Celgene Corporation, "Initial Phase I solid tumor data on Celgene's lead IMiD™, Revimid™," Press Release, Jun. 2001.
Celgene News Release, "Positive interim results presented at the VIIIth international myeloma workshop on Celgene Corporation's lead IMiD™ (REV/MID™)," May 8, 2001.
Celgene Press Release, "Initial phase I solid tumor data on Celgene's lead IMiD™, Revimid™," Jun. 2001.
Chan et al., Journal of Pharmaceutical Sciences, 1979, 68(7), 807-12.
Cheson et al., 2000, "Report of an international working group to standardize response criteria for myelodysplastic syndromes," Blood 96:3671-3674.
Christman, Oncogene, 2002, 21, 5483-95.
Chu et al., (2001) Principles of cancer management: Chemotherapy. In V.T. De Vita, Jr., S. Hellman, and S.A. Rosenberg (Eds): Cancer: Principles and Practice of Oncology (6 111 Ed.) Philadelphia: Lippincott Williams & Wilkins, Chapter 17.
Chu et al., "Principles of cancer management: Chemotherapy." In Cancer: Principles and Practice of Oncology, 6th Ed.; De Vita, Jr., Hellman, and Rosenberg Ed.; Lippincott Williams & Wilkins, Philadelphia, pp. 289-306 (2001).
Claessens et al., 2002, "In vitro proliferation and differentiation of erythroid progenitors from patients with myelodysplastic syndromes: evidence for Fas-dependent apoptosis," Blood 99:1594-1601.
International Search Report in PCT/US2011/035822 dated Aug. 29, 2011.
Official Action dated Feb. 10, 2009 in JP Application No. 2004-545192. (English translation provided.).
Partial European Search Report in corresponding EP Appl. No. 04821987.7 dated Mar. 23, 2009.
Written Opinion in PCT/US2011/035822 dated Aug. 29, 2011.
Corral et al., "Differential cytokine modulation and T cell activation by two distinct classes of thalidomide analogues that are potent inhibitors of TNF-alpha," J. Immunol. 163(1):380-386 (1999).
Corral et al., "Immunomodulation by thalidomide and thalidomide analogues," Ann. Rheum. Dis. 58(Suppl 1):I107-I113 (1999).
Corral et al., 1999, "Differential cytokine modulation and T cell activation by two distinct classes of thalidomide analogues that are potent inhibitors of TNF-alpha," J. Immunol. 163:380-386.
Corral et al., 1999, Ann. Rheum. Dis. 58(Supp. I):1107-1113.
Costa et al., 1998, Blood 92(10: suppl. 1):235b, Abstract #4007.
Cunningham et al., Cancer Chemotherapy Reports, Part I, 1974, 58(5), 677-81.
Curt et al., Cancer Research, 1985, 45, 3359-63.
D'Amato et al., "Mechanism of action of thalidomide and 3-aminothalidomide in multiple myeloma," Semin. Oncol. 28:597-601 (2001).
D'Amato et al., "Thalidomide is an Inhibitor of Angiogenesis", Proc. Natl. Acad. Sci. USA 91(9):4082-4085 (1994).
D'Amato et al., 1994, "Thalidoide is an inhibitor of angiogenesis," PNAS USA 91(9):4082-4085.
Dancey et al., "Neutrophil kinetics in man," J. Clin. Invest., 58(3):705-715 (1976).
Das et al., Molecular Cancer, 2006, 5(28), doi: 10.1186/1476-4598-5-28, available at http://www.molecular-cancer.com/content/5/1/28.
Davies et al., "Thalidomide and immunomodulatory derivatives augment natural killer cell cytotoxicity in multiple myeloma," Blood 98(1):210-216 (2001).
Davies et al., 2001, "Thalidomide and immunomodulatory derivatives augment natural killer cell cytotoxicity in multiple myeloma," Blood 98:210-216.
Davies et al., "Thalidomide (THAL) and Immunomodulatory Derivatives (IMiDS) Augment Natural Killer (NK) Cell Cytotocixity in Multiple Myeloma (MM)," Abstract #3617. American Society of Hematology, Dec. 1-5, 2000.
Deeg et al., 2002, "Soluble TNF receptor fusion protein (etanercept) for the treatment of myelodysplastic syndrome: a pilot study," Leukemia 16:162-164.
Devita et al., eds., "Plasma cell neoplasm." In Cancer Principles & Practice of Oncology, 5th Ed.; Lippincott-Raven Publishers, pp. 2344-2379 (1997).
Dexter, 1987, "Growth factors involved in haemopoiesis." J. Cell. Sci. 88 ( Pt 1):1-6.
Dexter, 1989, "Haemopoietic growth factors," Br. Med. Bull. 45(2):337-349.
Dimopoulos et al., "Thalidomide and dexamethasone combination for multiple myeloma refractory to dexamethasone-based reginens," Blood, 96(Supp):286b (2000).
Dimopoulos et al., "Thalidomide and dexamethasone combination for refractory multiple myeloma," Ann. Oncol. 12:991-995 (2001).
Dimopoulos, Blood, 96 Supp:286b (Abstract 4978) 2000.
Dishman et al., "Pharmacists' role in clozapine therapy at a Veterans Affairs medical center," Am. J. Hosp. Pharm. 51(7):899-901 (1994).
Dishman et al., "Pharmacists'ranscript role in clozapine therapy at a veterans affairs medical center," Am. J. Hosp. Pharm. 51:899-901 (1994).
Dourado, C. Mc., Seixas-Silva Jr., J.A., Besa, E.C., Response to thalidomide in 9 patients with myelodysplastic syndromes: A promising treatment for early or post-chemotherapy in late forms of MDS. Abstract #4855, American Society of Hematology, Dec. 1-5, 2000.
Dover et al., Blood, 1985, 66(3), 527-32.
Dredge et al., 2002, "Novel thalidomide analogues display antiangiogenic activity independently of immunomodulatory effects," Br. J. Cancer 87(10):1166-1172.
Durie and Stepan, "Efficacy of low dose thalidomide in multiple myeloma," Eur. J. Oncol. 1:1-8 (2000).
Edwards, D., "Thalidomide: Is there a silver lining?," Science News (1987) 131(13): 198.
Ehrenpreis et al., 1999, "Thalidomide therapy for patients with refractory Crohn's disease: an open-label trial," Gastroenterology 117(6):1271-1277.
Elliot et al., "The proteasome: A new target for novel drug therapies," Am. J. Clin. Pathol. 116:637-646 (2001).
Elliot et al., "The proteasome: a new target for novel drug therapies," Am. J. Clin. Pathol., 116(5):637-646 (2001).
Emens et al., 2001, "Chemotherapy: friend or foe to cancer vaccines?" Curr. Opin. Mol. Ther. 3(1):77-84.
Estey, E., Albitar, M., Cortes, J., Giles, F., Thomas, D., Koller, C., Beran, M., Kantarjian, H., Addition of thalidomide(T) to chemotherapy did not increase remission rate in poor prognosis AML/MDS. Abstract #1394, American Society of Hematology, Dec. 1-5, 2000.
Fabbri, A., Biscardi, M., Innocenti, F., Balestri, G., Gavazzi, S., Bellesi, G., Grossi, A., Thalidomide in combination with Amifostine in the treatment of MDS: evaluation of clinical and laboratory findings. Abstract #4819, American Society of Hematology, Dec. 7-11, 2001.
FDA Meeting Minutes which contain a statement from a Dr. Holmes, said to represent the American College of Medical Genet-

(56) References Cited

OTHER PUBLICATIONS ics and the Teratology Society. (Transcript of the Forty-Seventh Meeting of the Dermatologic and Ophthalmic Drugs Advisory Committee, at 137 (Sep. 4, 1997)).
Fenaux et al., "Azacitidine (AZA) Treatment Prolongs Overall Survival (OS) in Higher-Risk MDS Patients Compared with Conventional Care Regimens (CCR): Results of the AZA-001 Phase III Study," Blood, 2007, 110(11), Part I, 250A-251A (American Society of Hematology, Annual Meeting and Exposition, Dec. 8-11, 2007, Abstract #817).
Fenaux et al., "Azacitidine Prolongs Overall Survival Compared with Conventional Care Regimens in Elderly Patients with Low Bone Marrow Blast Count Acute Myeloid Leukemia," Journal of Clinical Oncology, 2010, 28(4), 562-69.
Fenaux et al., "Effect of Azacitidine (AZA) vs. Low-Dose Ara-C (LDAC) on Overall Survival (OS), Hematologic Response, Transfusion Independence, and Safety in Patients (PTS) with Higher-Risk Myelodysplastic Syndromes (MDS)," Haematologica—The Hematology Journal, 2008, 93(Suppl. 1), p. 90 (13th Congress of the European Hematology Association, Jun. 12-15, 2008, Abstract #0224).
Fenaux et al., "Efficacy of Azacitidine compared with that of conventional care regimens in the treatment of higher-risk myelodysplastic syndromes: a randomized, open-label, phase III study," The Lancet Oncology, 2009, 10(3), 223-32 (published electronically Feb. 2009, pp. 1-10, doi:10.1016/S1470-2045(09)70003-8).
Fenaux et al., "Prolonged Survival with Improved Tolerability in Higher-Risk Myelodysplastic Syndromes: Azacitidine Compared with Low Dose Ara-C," Br. J. Haematol, 2010, 149:244-249.
Figg et al., "Pharmacokinetics of thalidomide in an elderly prostate cancer population," J. Pharm. Sci., 88:121-125 (1999).
Filella et al., "Cytokines (IL-6, TNF-alpha, IL-1 alpha) and soluble interleukin-2 receptor as serum. tumor markers in multiple myeloma," Cancer Detect. Prev. 20:52-56 (1996).
Fillella et al., "Cytokines (IL-6, TNF-alpha, IL-lalpha) and soluble interleukin-2 receptor as serum tumor markers in multiple myeloma," Cancer Detect. Prev.,20(1):52-56 (1996).
Foerster et al., "Effects of thalidomide and EM12 on the synthesis of TNF-α in coclutures of human monocytes and lymphocytes," Abstract 517 (1995).
Gahrton et al., "Progress in haematopoietic stem cell transplantation for multiple myeloma," J. Intern. Med., 248(3):185-201 (2000).
Garcia-Manero, Current Opinion in Oncology, 2008, 20, 705-10.
Gardner et al., "Assessing the Effectiveness of a Computerized Pharmacy System," in Decision Support Systems in Critical Care, (M.M. Shabot et al., eds.,) pp. 174-183 (1994).
Gersuk et al., 1996, "Fas (CD95) receptor and Fas-ligand expression in bone marrow cells from patients with myelodysplastic syndrome," Blood 88(3):1122-1123.
Gifford et al., Clinical Cancer Research, 2004, 10, 4420-26.
Glasmacher et al., "Oral idarubicin, dexamethasone and vincristine (VID) in the treatment of multiple myeloma," Leukemia, 11(Suppl. 5):522-826 (1997).
Goemer et al., 2002, Morbidity and mortality of chronic GVHD after hematopoetic stem cell transplantation from HLA-identical siblings for patients with aplastic or refractory anemias, Biology of Blood and Marrow Transplantation (Abstract only) 8(1):47-56, accessed from Database STN/CAPLUS, Fred Hutchinson Cancer Research Center and the University of Washington, Seattle, WA, Accession No. 2002:1195127.
Goldberg et al., 1990, "Survey of exposure to genotoxic agents in primary myelodysplastic syndrome: correlation with chromosome patterns and data on patients without hematological disease," Cancer Res. 50(21):6876-6881.
Goldberg et al., 2003, "Myelodysplastic subclones in chronic myeloid leukemia: implications for imatinib mesylate therapy," Blood 101:781.
Golde et al., 1988, "Hormones that stimulate the growth of blood cells," Sci. Am. 259(1):62-71.

Greenberg et al., 1997, "International scoring system for evaluating prognosis in myelodysplastic syndromes," Blood 89(6):2079-2088.
Grinblatt et al., "AVIDA: A Longitudinal Registry of Clinical and Quality of Life Outcomes in Patients with Hematologic Disorders Receiving Azacitidine," Blood, 2007, 110(11), Part II, 223B. (American Society of Hematology, 49th Annual Meeting, Dec. 8-11, 2007, Abstract #4605).
Grinblatt et al., "Usage patterns and Transfusion Requirements in Patients Enrolled in AVIDA, A Longitudinal Registry of Patients with Hematologic Disorders Receiving Azacitidine," Haematologica—The Hematology Journal, 2008, 93(Suppl. 1), p. 281 (13th Congress of the European Hematology Association, Jun. 12-15, 2008, Abstract #699).
Grönroos et al., "A medication database—a tool for detecting drug interactions in hospital," Eur. J. Clin. Pharmacol., 53(1): 13-17 (1997).
Gupta et al., 2001, "Adherences of multiple myeloma cells to bone marrow stromal cells upregulates vascular endothelial growth factor secretion: therapeutic applications," Leukemia 15:1950-1961.
Gupta et al., "Adherence of multiple myeloma cells to bone marrow stromal cells upregulates vascular endothelial growth factor secretion: therapeutic applications," Leukemia 15(12):1950-1961 (2001).
Hamera et al., "Alcohol, Cannabis, Nicotine, and Caffeine Use and Symptom Distress in Schizophrenia," J. Nerv. Ment. Dis. 183(9):559-565 (1995).
Handman et al., 1979, "Stimulation by granulocyte-macrophage colony-stimulating factor of Leishmania tropica killing by macrophages," J. Immunol. 122(3):1134-1137.
Harris et al., 1999, "World Health Organization classification of neoplastic diseases of the hematopoietic and lymphoid tissues: report of the Clinical Advisory Committee meeting—Airlie House, Virginia, Nov. 1997," J. Clin. Oncol. 17(12):3835-3849.
He, W., et al., 1993, Abstract of papers, 206th American Chemical Society, Chicago, IL; Med. Chem., paper 216.
Hegeret al., "Embryotoxic Effects of Thalidomide Derivatives in the Non-Human Primate Callithrixjacchus. IV Teratogenicity of μg/kg Doses of the EMJ 2 Enantiomers," Teratogenesis, Carcinogenesis, and Mutagenenesis (1994) 4(3):115-122.
Hellstrom et al., 1990, 76(Supp. 1):279a.
Hellstrom-Lindberg et al., 1997, "Erythroid response to treatment with G-CSF plus erythropoietin for the anaemia of patients with myelodysplastic syndromes: proposal for a predictive model," Br. J. Haematol. 99:344-351.
Hideshima et al. 2000, "Thalidomide and its analogs overcome drug resistance of human multiple myeloma cells to conventional therapy," Blood 96(9):2943-2950.
Hideshima et al., "Novel therapies targeting the myeloma cell and its bone marrow microenvironment," Semin. Oncol., 28(6):607-612 (2001).
Hideshima et al., "The proteasome inhibitor PS-341 inhibits growth, induces apoptosis, and overcomes drug resistance in human multiple myeloma cells," Cancer Res. 61(7):3071-3076 (2001).
Hideshima et al., "Thalidomide and its analogs overcome drug resistance of human multiple myeloma cells to conventional therapy," Blood 96(9):2943-2950 (2000).
Hideshima, T., Chauhan, D., Castro, A., Hayashi, T., Mitsiades, C., Mitsiades, N., Akiyama, M., Richardson, P.G., Schlossman, R.L., Adams, J., Anderson, K.C., NF-KB as a Therapeutic Target in Multiple Myeloma (MM). Abstract #1581. American Society of Hematology, Dec. 7-11, 2001.
Hideshima, T., Chauhan, D., Shima, Y., Noopur, R., Davies, F.E., Tai, Y., Treon, S.P., Lin, B.K., Schlossman, R.L., Richardson, P.G., Gupta, D., Muller, G.W., Stirling, D.I., Anderson, K.C., Thalidome (THAL) and its Analogs Overcome Drug Resistance of Human Multiple Myeloma (MM) Cells to Conventional Therapy. Abstract #1313. American Society of Hematology, Dec. 1-5, 2000.
Hochster et al., "Activity and pharmacodynamics of 21-Day topotecan infusion in patients with ovarian cancer previously treated with platinum-based chemotherapy. New York Gynecologic Oncology Group," J. Clin. Oncol. 17(8):2553-2561 (1999).
Holsinger et al., "Therapy of Myelodysplastic Syndrome (MDS) with Azacitidine Given in Combination with Etanercept : A Phase

(56) References Cited

OTHER PUBLICATIONS

II Study," Blood, 2007, 110(11), Part I, 435A (American Society of Hematology, Annual Meeting, Dec. 8-11, 2007, Abstract #1452).
Hus et al., "Thalidomide treatment of resistant or relapsed multiple myeloma patients," Haematologica 86(4):404-408 (2001).
International Search Report in PCT/US2008/012430 dated Mar. 16, 2009.
International Search Report, for PCT/US2009/002999, dated Sep. 14, 2009.
International Search Report for PCT/US2003/011323.
Israili et al., Cancer Research, 1976, 36, 1453-61.
Jabbour et al., "Efficacy of Azacytidine (5-AC) Given as Maintenance or Salvage Therapy for Patients (pts) with Acute Leukemia Post Allogeneic Stem Cell Transplantation (HSCT)," Blood, 2007, 110(11), Part I, 885A (American Society of Hematology, 49th Annual Meeting, Dec. 8-11, 2007, Abstract #3013).
Jaffe et al., eds., 2001, "World Health Organization classification of tumours: pathology and genetics of tumours of haematopoietic and lymphoid tissues," Lyon, France: IARC Press pp. 61-74.
Jagannath et al., "Pomalidomide (POM) with or without low-dose dexamethasone (LoDEX) in patients (Pts) with relapsed and refractory multiple myeloma (RRMM): MM-002 phase II age subgroup analysis," J. Clin. Oncol. 31, Abstrct # 8532, (2013).
Jönsson, "Chemical structure and teratogenic properties. 3. A review of available data on structure-activity relationships and mechanism of action of thalidomide analogues," Acta. Pharm. Suec. 9:521-542 (1972).
Jordan et al., New England Journal of Medicine, 2006, 355(12), 1253-61.
Jourdan et al., "Tumor necrosis factor is a survival and proliferation factor for human myeloma. cells," Eur. Cytokine Netw. 10(1):65-70 (1999).
Jubb, et al., Journal of Pathology, 2001, 195, 111-34.
Kaminskas et al., "Approval Summary. Azacitidine for Treatment of Myelodysplastic Syndrome. Subtypes," Clinical Cancer Research, 2005, 11(10), 3604-08.
Kaplan et al., 1958, "Nonparametric estimation from incomplete observations," J. Am. Stat. Assoc. 53:457-481.
Keravich et al., "Challenges of thalidomide distribution in a hospital setting," Am. J. Health Syst. Pharm., 56(17):1721-1725 (1999).
Kibbe ed., Handbook of Pharmaceutical Excipients, 3rd edition, pp. 160-162 (2000).
Kitagawa et al., 1997, "Overexpression of tumor necrosis factor (TNF)-a and interferon (INF)-g by bone marrow cells from patients with myelodysplastic syndromes," Leukemia 11:2049-2054.
Knight, "Cancer patients ahead of FDA on thalidomide use," Washington Post Jun. 25, 2001.
Koch, 1985, "Thalidomide and congeners as anti-inflarmnatory agents," Prog. Med. Chem. 22:165-242.
Kon-nichi no Chiryou Shishin, 1997 [Pocket Edition], Igaku Shoin, 1997, 513-514 (in Japanese).
Kornblith et al., Journal of Clinical Oncology, 2002, 20(10), 2441-52.
Kosten et al., "Substance Abuse and Schizophrenia: Editors' Introduction," Schizophrenia Bulletin, 23(2): 181-186 (1997).
Kropff, 2000, Blood 96(11 part 1):168a.
Kurland et al., 1979, "Induction of prostaglandin E synthesis in normal and neoplastic macrophages: role for colony-stimulating factor(s) distinct from effects on myeloid progenitor cell proliferation," Proc. Natl. Acad. Sci. USA 76(5):2326-2330.
Kurzrock, 2002, "Myelodysplastic syndrome overview," Seminars in Hematology (Abstract only) (Suppl. 2) 39(3).
Kyle et al., "Therapeutic Application of Thalidomide in Multiple Myeloma," Semin. Oncol. 28(6):583-587 (2001).
Lacy et al., "Pomalidomide (CC4047) plus low-dose dexamethasone as therapy for relapsed multiple myeloma," J. Clin. Oncol. 27(30):5008-5014 (2009).
Lacy et al., "Pomalidomide plus low-dose dexamethasone in myeloma refractory to both bortezomib and lenalidomide: comparison of 2 dosing strategies in dual-refractory disease," Blood 118(11):2970-2975 (2011).
Lee et al., "A pilot trial of hyperfractionated thoracic radiation therapy with concurrent cisplatin and oral etoposide for locally advanced inoperable non-small-cell lung cancer: a 5-year follow-up report," Int. J. Radiat. Oncol. Biol. Phys., 42(3):479-486 (1998).
Lentsch, S., Rogers, M., Leblanc, R., Birsner, A., Shah, J., Anderson K., D'Amato R., 3-Amino-Phthalimido-Glutarimide (S-3APG) Inhibits Angiogenesis and Growth in Drug Resistant Multiple Myeloma (MM) in vivo. Abstract #1976, American Society of Hematology, Dec. 7-11, 2001.
Lentzsch et al., "S-3-amino-phthalimido-glutarimide inhibits angiogenesis and growth of B-cell neoplasias in mice," Cancer Research 62:2300-2305 (2002).
Lentzsch et al., 2003, "Immunomodulatory analogs of thalidomide inhibit growth of Hs Sultan cells and angiogenesis in vivo," Leukemia 17(1):41-44.
Li et al., "MethPrimer: Designing Primers for Methylation PCRs," Bioinformatics, 2002, 18(11), 1427-31.
Li et al., Cancer Research, 1970, 30, 2770-75.
Lin et al., Journal of Pharmaceutical Sciences, 1981, 70(11), 1228-32.
Linnarsson, "Decision support for drug prescription integrated with computer-based patient records in primary care," Med. Inform., 18(2):131-142 (1993).
Lipkin, R., "Deriving new drugs from thalidomide," Science News (1995) 148: 171.
Lisak, L.A., Little, L., Dean, L., Ekbal, M., Durandt, M., Hussain, M., Kaistha, V., Raza, A., Delayed responses to thalidomide in patients with myelodysplastic syndromes. Abstract #4861, American Society of Hematology, Dec. 1-5, 2000.
List et al., "Myelodysplastic Syndromes," Hematology, American Society of Hematology, Education Program Book, 2004, 297-317.
List et al., 2004, "Myelodysplastic syndromes," Wintrobe's Clinical Hematology, 11th ed., Philadelphia: Lippincott Williams & Wilkins pp. 2207-2234.
List et al., 2004, "Vascular endothelial growth factor receptor-1 and receptor-2 initiate a phosphatidylinositide 3-kinase-dependent clonogenic response in acute myeloid leukemia cells," Exp. Hematol. 32:526-535.
List et al., 2005, "Efficacy of Lenalidomide in myelodysplastic syndromes," N. Engl J Med. 352(6):549-557.
List, 2002, ASH Abstract #521.
List, AF; "New Approaches to the Treatment of Myelodysplastia," The ONcologist 2002; 7 Suppl. 1:39-49.
List, AF; Pharmacological Differentiation and Anti-Apoptic Therapy in Myelodysplastic Syndromes; "Forum Trends in Experimental and Clinical Medicine," 9:35-45,1999.
List, AF; Brasfield, F.; Heaton, R.; Glinsmann-Gibson, B.; Crook, L.; Taetle, R.; Capizzi, R.;. Stimulation of Hematopoiesis by Amifostine in Paitents with Myelodysplattic Syndrom. Blood 1997; 90(9): 3364-9.
List, Alan F. et al., "Efficacy and Safety of CC5013 for Treatment of Anemia in Patients with Myelodysplastic Syndromes (MDS)," Blood, 2003, 102(11):184a Abstract #641.
List, Alan F. et al., "High Erythropoietic Remitting Activity of the Immunomodulatory Thalidomide Analog, CC5013, in Patients with Myelodysplastic Syndrome (MDS)," Blood, 2002, 100(11):96a Abstract #353.
Lomen et al., Cancer Chemotherapy Reports, Part I, 1975, 59(6), 1123-26.
Lubbert, M, "DNA Methylation Inhibitors in the Treatment of Leukemias, Myelodysplastic Syndromes and Hemoglobinopathies: Clinical Results and Possible Mechanisms of Action," Current Topics in Microbiology and Immunology, 2000, 249:135-164.
Lyons et al., "Hematologic Improvement, Transfusion Independence, and Safety Assessed Using Three Alternative Dosing Schedules of Azacitidine in Patients with Myelodysplastic Syndromes," Blood, 2006, 108(11), Part I, 752A (American Society of Hematology, 48th Annual Meeting, Dec. 9-12, 2006, Abstract #2662).

(56) References Cited

OTHER PUBLICATIONS

Lyons et al., "Hematologic Response to Three Alternative Dosing Schedules of Azacitidine in Patients with Myelodysplastic Syndromes," Journal of Clinical Oncology, 2009, 27(11), 1850-56.
Maciejewski et al., 2002, "A pilot study of the recombinant soluble human tumour necrosis factor receptor (p75)-Fc fusion protein in patients with myelodysplastic syndrome," Br. J. Haematol. 117:119.
Mann et al., "Passage of chemicals into human and animal semen: mechanisms and significance," Crit. Rev. Toxicol., 11(1):1-14 (1982).
Marcucci et al., "Bioavailability of Azacitidine Subcutaneous Versus Intravenous in Patients with the Myelodysplastic Syndromes," Journal of Clinical Pharmacology, 2005, 45(5), 597-602.
Market Letter (Oct. 15, 2001), "Celgene's Revlimid an orphan drug, says FDA," Market Publications Ltd. ("October Market Letter").
Marriott et al., "Immunotherapeutic and antitumour potential of thalidomide analogues," Expert. Opin. Biol. Ther. 1:1-8 (2001).
Marriott et al., 2001, "Immunothempeutic and antitumour potential of thalidomide analogues," Expert Opin. Biol. Ther. 1(4):675-682.
Marwick, "Thalidomide back—under strict control," JAMA, 278(14):1135-1137 (1997).
McCann, 1999, Drug Topics pp. 41-42 (Jun. 21, 1999).
Melchert, Magda, et al., "The thalidomide saga," The International Journal of Biochemistry & Cell Biology, Jul. 2007, 39:1489-1499.
Menill, "Substance Abuse and Women on Welfare," National Center on Addiction and Substance Abuse at Columbia University, Jun. 1994.
Menill, J.C., Substance Abuse and Women on Welfare, National Center on Addiction and Substance Abuse at Columbia University, Jun. 1994.
Merck Manual 17th ed. Japanese version, 1999, 951-952.
Metcalf, 1985, "The granulocyte-macrophage colony-stimulating factors," Science 229(4708):16-22.
Mitchell et al., "A pregnancy-prevention program in women of childbearing age receiving isotretinoin," N. Engl. J. Med., 333(2):101-106 (1995).
Mitsiades et al., "Concepts in the use of TRAIL/Apo2L: an emerging biotherapy for myeloma and other neoplasias," Expert Opin. Investig. Drugs, 10(8):1521-1530 (2001).
Mitsiades et al., "Apoptic signaling induced by immunomodulatory thalidomide analogs in human multiple myeloma cells: therapeutic implications," Blood, 2002, 99:4525-4530, American Society of Hematology.
Mitsiades, N., Mitsiades, C., Poulaki, V., Akiyama, M., Tai, Y., Lin, B., Hayashi, T., Catley, L., Hideshima, T., Chauhan, D., Treon, S.P., Anderson, K.C., Apoptotic Signaling Induced by Immunomodulatory Thalidomide Analogs (Imids) in Human Multiple Myeloma Cells; Therapeutic Implications. Abstract #3224. American Society of Hematology, Dec. 7-11, 2001.
Moertel et al., Cancer Chemotherapy Reports, Part I, 1972, 56(5), 649-52.
Mojaverian et al., Journal of Pharmacy and Pharmacology, 1984, 36, 728-33.
Moller et al., 1997, "Inhibition of IL-12 production by thalidomide," J. Immunol. 159(10).5157-5161.
Montero et al., "Economic study of neutropenia induced by myelotoxic chemotherapy," Pharm. World Sci., 16(4):187-192 (1994).
Moore et al., 1980, "Production of lymphocyte-activating factor (Interleukin 1) by macrophages activated with colony-stimulating factors," J. Immunol. 125(3):1302-1305.
Moore, 1991, "The clinical use of colony stimulating factors," Ann. Rev. Immunol. 9:159-191.
Moreira et al., 1993, "Thalidomide exerts its inhibitory action on tumor necrosis factor alpha by enhancing mRNA degradation," J. Exp. Med. 177:1675-1680.
Morgan et al., "Lenalidomide (Revlimid), in combination with cyclophosphamide and dexamethasone (RCD), is an effective and tolerated regimen for myeloma patients," Br. J. Haematol., 137(3):268-269 (2007).
Muller et al., "Amino-substituted thalidomide analogs: potent inhibitors of TNF-α production," Bioorg. Med. Chem. Lett. 9(11):1625-1630 (1999).
Muller et al., 1996, "Structural modifications of thalidomide produce analogs with enhanced tumor necrosis factor inhibitory activity," J. Med. Chem. 39(17):3238-3240.
Muller et al., 1998, "Thalidomide analogs and PDE4 inhibition," Bioorg. Med. Chem. Lett. 8(19):2669-2674.
Muller, G.M., Thalidomide: From tragedy to new drug discovery, Chemtech (1997) 27(1) 21-25.
Muller, Thalidomide: From tragedy to new drug discovery, Chemtech 27:21-25 (1997).
Mundle, S., Zorat, F., Shetty, V., Allampallam, K., Alvi, S., Lisak, L., Little, L., Dean, L., Nascimben, F., Ekbal, M., Duraudt, M., Broderick, E., Venugopal, P., Raza, A., Thalidomide in myelodysplasia. Abstract #626, American Society of Hematology, Dec. 1-5, 2000.
Mundt, "Interactive Voice Response Systems in Clinical Research and Treatment," Psychiatr. Serv. 48(5):611-612, 623 (1997).
Munshi et al., 1999, Blood 94(10 part 1):578a.
Musto, P., Falcone, A., Bodenizza, C., Sanpaolo, G., Matera, R., Bisceglia, M., Carella, A.M., Thalidomide (THAL) significantly improves anemia in selected transfusion-dependent patients with myelodysplastic syndromes (MDS): relationship to serum and marrow levels of angiogenetic growth factors (AGF). Abstract #2606, American Society of Hematology, Dec. 7-11, 2001.
N. Ake Jonnson, 1972, "Chemical Structure and Teratogenic Properties," Acta Pharm., pp. 521-542.
National Cancer Institute, Common Toxicity Criteria Manual, Ver. 2.0, Jun. 1, 1999.
NCT00480363: "QUIREDEX: Revlimid (lenalidomide) and dexamethasone (ReDex) treatment versus observation in patients with smoldering multiple myeloma with high risk of progression (QUIREDEX)."
Neil et al., Cancer Chemotherapy Reports, Part I, 1975, 59(3), 459-65.
Neuwirtova, R. et al., "Immunomodulatory therapy of low-risk myelodysplastic syndromes," Onkologie, 2000, 23(7):82 Abstract #0305.
Noguelra et al., "Effect of thalidomide and some derivatives on the adhesion of lymphocytes to endothelial cells," Abstract 518 (1995).
NORD Honors Celgene Corporation for Development of THALOMID(R) (thalidomide), PR Newswire at 1-2 (1999).
Notari et al., Journal of Pharmaceutical Sciences, 1975, 64(7), 1148-57.
Ogawa, 1989, "Hemopoietic stem cells: stochastic differentiation and humoral control of proliferation," Environ. Health Perspect. 80:199-207.
Okamoto, T., Kotsuzuiikeisei Shoukougun to Men-eki Ijo, Bessatsu Nihon Rinsho, Syndrome Series for each area, No. 22, Blood Syndromes III, Nihon Rinshou, 213-216 (in Japanese).
Olson et al., "Thalidomide (N-phthaloylglutamimide) in the treatment of advanced cancer," Clinical Pharmacology and Therapeutics 6(3):292-297 (1965).
Palumbo et al., "Low-dose thalidomide plus dexamethasone is an effective salvage therapy for advanced myeloma." Haematologica 86(4):399-403 (2001).
Park, Y., Kim, S.A., Kim, C.J., Chung, J.H., Mechanism of the Effect of Thalidomide on Human Multiple Myeloma Cells. Abstract #2685. American Society of Clinical Oncology, May 12-17, 2001.
Pastuszak et al., "Use of the retinoid pregnancy prevention program in Canada: Patterns of contraception use in women treated with isotretinoin and etretinate," Reprod. Toxicol. 8:63-68 (1994).
Payvandi et al., 2003, ASCO Abstract #992.
Payvandi, F., Wu, L., Gupta, D., Hideshima, T., Haley, M., Muller, G., Chen, R., Anderson, K.C., Stirling, D., Effects of a Thalidomide Analog on Binding Activity of Transcription Factors and Cell Cycle Progression of Multiple Myeloma Cell Lines. Abstract #2487. American Society of Hematology, Dec. 1-5, 2000.
Payvandi, F., Wu, L., Haley M., Gupta, D., Zhang, L., Schafer, P., Muller, G.W., Chen, R., Anderson, K.C., Stirling, D., Thalidomide Analogs IMiDS Inhibit Expression of Cyclooxygenase-2 in Multiple Myeloma Cell Line and LPS Stimulated PBMCs. Abstract #2689. American Society of Hematology, Dec. 7-11, 2001.

(56) References Cited

OTHER PUBLICATIONS

Peddie et al., 1997, "Oxidative DNA damage in CD34+ myelodysplastic cells in associated with intracellular redox changes and elevated plasma tumor necrosis factor-α concentration," Br. J. Haematol. 99:625-631.
Penichet et al., 2001, "Antibody-cytokine fusion proteins for the therapy of cancer," J. Immunol. Methods. 248(1-2):91-101.
Perry, Michael C. ed., The Chemotherapy Source Book (1992).
Pestotnik et al., "Therapeutic Antibiotic Monitoring: Surveillance Using a Computerized Expert System," Am. J. Med. 88(1):43-48 (1990).
Phillips et al., "Up-Regulation of miR-195 Expression Leads to Decreased Expression of Basic Fibroblast Groth Factor in CLL Patients Treated with DNA Methylation Inhibitors," Blood, 2007, 110(11), Part I, 935A (American Society of Hematology, Annual Meeting, Dec. 8-11, 2007, Abstract #3183).
Physicians' Desk Reference, 2002, 56the ed. pp. 582-592, 1154-1158, 1755-1760.
Piper et al., "Anti-inflammatory immunosuppressive thalidomide analogs. Screening," Int. J. Leprosy, 49:511-512 (1981).
Platzbecker, U. et al., "A Phase I Study of a Combination of 5-Azacytidine Followed by Lenalidomide in High-Risk MDS or AML Patients with Chromosome 5 Abnormalities—Interim Results of the 'Azale' Trial," Blood (ASH Annual Meeting Abstracts), 2010, 116: Abstract 4000.
Powell et al., "Guideline for the Clinical Use and Dispensing of Thalidomide," Postgmd. Med. J. 70(830):901-904 (1994).
Press Release, "New Data Validate Vidaza® Response Rates in MDS and Report Results in AML," Medical News Today, Dec. 26, 2006, available at http://www.medicalnewstoday.com/articles/58992.php.
Press Release, "Vidaza® Significantly Extends Overall Survival by 74% in Phase 3 Trial in Myelodysplastic Syndromes (MDS)," Medical News Today, Aug. 3, 2007, available at http://www.medicalnewstoday.com/articles/78660.php.
Quagliana et al., Cancer Treatment Reports, 1977, 61(1), 51-54.
Quiredex: Revlimid (Lenalidomide) and Dexamethasone (ReDex) Treatment Versus Observation in Patients With Smoldering Multiple Myeloma With High Risk of Progression retrieved on the internet https://clinicaltrials.gov/ct2/show/NCT00480363?term=NCT00480363&rank=1>. (NCT00480363 on Nov. 26, 2008 at ClinicalTrials.gov).
Rajapaksa et al., 1996, Altered oncoprotein expression and apoptosis in myelodysplastic syndrome marrow cells,: Blood 88:4275-4287.
Raje et al., "Thalidomide—a revival story," N. Engl. J. Med. 341(21):1606-1609 (1999).
Rajkumar et al., "Thalidomide in the treatment of plasma cell malignancies," J. Clin. Oncol. 19(16):3593-3595 (2001).
Rajkumar et al., "Lenalidomide plus high-dose dexamethasone versus lenalidomide plus low-dose dexamethasone as initial therapy for newly diagnosed multiple myeloma: an open-label randomised controlled trial," The Lancet, 11:29-37 (2010).
Rajkumar et al., "Phase III trial of lenalidomide plus highdose dexamethasone versus lenalidomide plus low-dose dexamethasone in newly diagnosed multiple myeloma (E4A03): A trial coordinated by the Eastern Cooperative Oncology Group," J. Clin. Oncol. 25:18S (2007).
Rajkumar et al., "Phase III trial of lenalidomide plus highdose dexamethasone versus lenalidomide plus low-dose dexamethasone in newly diagnosed multiple myeloma (E4A03): A trial coordinated by the Eastern Cooperative Oncology Group," J Clinical Oncology, 2007 ASCO Annual Meeting Proceedings, vol. 25, No. 18S (Jun. 20 Supplement), 2007, LBA8025.
Rajkumar et al., "Thalidomide plus dexamethasone (Thal/Dex) and thalidomide alone (Thal) as first line therapy for newly diagnosed myeloma (MM)," Blood 96(Supp.):168 (2000).
Rajkumar et al., "Thalidomide Plus Dexamethasone (Thal/Dex) and Thalidomide Alone (Thal) as First Line therapy for Newly Diagnosed Myeloma (MM)," Blood, 96 Supp. Nov. 2000, p. 167a Abstract 722.
Rajkumar et al., "Combination therapy with lenalidomide plus dexamethasone (Rev/Dex) for newly diagnosed myeloma," Blood, Dec. 15, 2005, 106 (13)4050-4053.
Rajkumar et al., "Thalidomide in the treatment of plasma cell malignancies," J. Clin. Oncol. 19:3593-3595 (2001).
Rajkumar, "Thalidomide in Multiple Myeloma," Oncology (Williston Park) 14(12 Suppl. 13):11-16 (2000).
Ramanarayanan, J. et al., "Abrogation of tumor necrosis alpha (TNF-alpha) pathway by anti-TNF therapy in hematological malignancies," J. Clin. Oncol., 2009, 27:15s Abstract #7093.
Ratain, "Pharmacology of Cancer Chemotherapy," Chapter 19, p. 381 (2001).
Ratain, "Pharmacology of Cancer Chemotherapy." In Cancer: Principles & Practice of Oncology, pp. 335-459 (2001).
Raza et al., 1995, "Apoptosis in bone marrow biopsy samples involving stromal and hematopoietic cells in 50 patients with myelodysplastic syndromes," Blood 86:268-276.
Raza et al., 2001, "Thalidomide Produces Transfusion Independence in Long-standing Refractory Anemias of Patients with Myelodysplastic Syndromes," Blood 98(4):958-965.
Raza, A., Dull, D., Lisak, L., Dean, L., Fantroy, L., Gezer, S., Ali, E., Goldberg, C., Loew, J., Hsu, W-T., Venugopal, P., Combination of thalidomide and enbrel for the treatment of patients with myelodysplastic syndromes (MDS). Abstract #4831. American Society of Hematology, Dec. 7-11, 2001.
Raza, A., Lisak, L., Andrews, C., Little, L., Muzammil M., Alvi, S., Mazzoran, L., Zorat, F., Akber, A., Ekbal, M., Razvi, S., Venugopal, P., Thalidomide produces transfusion independence in patients with long-standing refractory anemias and myelodysplastic syndromes (MDS). Abstract #2935, Amer. Soc. of Hematology, Dec. 3-7, 1999.
Raza, A., Lisak, L., Andrews, C., Little, L., Zorat, F., Shetty, V., Alvi, S., Mundle, S., Allampallam, K., Durandt, M., Ekbal, M., Muzammil, M., Encouraging improvement in cytopenias of patients with myelodysplastic syndromes (MDS) with thalidomide. Abstract #111, Amer. Soc. of Clinical Oncology, May 20-23, 2000.
Raza, A., Lisak, L., Dutt, D., Dean, L., Fantroy, L., Ali, E., Gezer, S., Hsu, W-T., Goldberg, C., Loew, J., Venugopal, P., Combination of thalidomide with pentoxifylline, ciprofloxacin, and dexamethasone (PCD) in patients with myelodysplastic syndromes (MDS). Abstract #4830, American Society of Hematology, Dec. 7-11, 2001.
Raza, A., Lisak, L., Little, L., Dean, L., Gezer, S., Venugopal, V., Summary and future direction of anti-tumor necrosis factor (TNF) therapies in myelodysplastic syndromes (MDS). Abstract #2700, American Society of Hematology, May 12-17, 2001.
Raza, A., Lisak, L., Little, L., Ekbal, M., Durandt, M., Ali, E., Nascimben, F., Tareen, M., Venugopal, P., Thalidomide as a single agent or in combination with topotecan, pentoxifylline and/or enbrel in myelodysplastic syndromes (MDS). Abstract #627, American Society of Hematology, Dec. 1-5, 2000.
Reiman et al., "Meeting Synopsis, VIII International Myeloma Workshop, Banff Springs Hotel, Banff, Alberta, Canada, May 4-8, 2001," Eur. J. Haematol. 67(3):199-202 (2001).
Reiman et al., "Meeting synopsis, VIII International Myeloma Workshop, Banff Springs Hotel, Banff, Alberta, Canada, May 4-8, 2001," Eur. J. Haematol. 67:199-202 (2001).
Richardson et al., "A randomized phase 2 study of lenalidomide therapy for patients with relapsed or relapsed and refractory multiple myeloma," Blood 108:3458-3464 (2006).
Richardson et al., "Thalidomide in multiple Myeloma," Biomed. Pharmacother. 56(3):115-128 (2002).
Richardson et al., "Thalidomide: Emerging Role in Cancer Medicine," Ann Rev. Med. 53:629-657 (2002).
Richardson et al., "A phase 1/2 multi-center, randomized, open label dose escalation study to determine the maximum tolerated dose (MTD), safety, and efficacy of pomalidomide (POM) alone or in combination with low-dose dexamethasone (DEX) in patients (PTS) with relapsed and refractory multiple myeloma (RRMM) who have received prior treatment (TX) that includes lenalidomide (LEN) and bortezomib (BORT)," Haematologica, 96:S31 (2011).

(56) References Cited

OTHER PUBLICATIONS

Richardson et al., "Immunomodulatory drug CC-5013 overcomes drug resistance and is well tolerated in patients with relapsed multiple myeloma," Blood, 2002 100:3063-3067, American Society of Hematology.
Richardson et al., 2002, "Immunmodulatmy dmg CC-5013 overcomes dmg resistance and is well tolerated in patients with relapsed multiple myeloma," Blood 100:3063-3067.
Richardson, P.G. et al., A Phase 1/2 Multi-Center, Randomized, Open Label Dose Escalation Study to Determine the Maximum Tolerated Dose (MTD), Safety, and Efficacy of Pomalidomide (POM) Alone or in Combination with Low-Dose Dexamethasone (DEX) in Patients (PTS) with Relapsed and Refractory Multiple Myeloma (RRMM) Who Have Received Prior Treatment (TX) That Includes Lenalidomide (LEN) and Bortezomib (BORT), Haematologica, 2001; 96(s1):S31, Abstract O-12, 13th International Myeloma Workshop, Paris, France—May 3-6, 2011.
Richardson, P.G., Schlossman, R.L., Hideshima, T., Davies, F., Leblanc, R., Catley, L., Doss, D., Kelly, K.A., Mckenney, M., Mechlowicz, J., Freeman, A,. Deocampo, R., Rich, R., Ryoo, J., Chauhan, D., Munshi, N., Weller, E., Zeldis, J., Anderson, K.C., A Phase 1 Study of Oral CC5013, an Immunomodulatory Thalidomide (Thal) Derivative, in Patients With Relapsed and Refractory Multiple Myeloma (MM). Abstract #3225. American Society of Hematology, Dec. 7-11, 2001.
Robert et al., "Phase 1 and pharmacologic study of 7- and 21-day continuous etoposide infusion in patients with advanced cancer," Cancer Chemother. Pharmacol., 38(5):459-465 (1996).
Rose et al., 1995, "The use of r-HuEpo in the treatment of anaemia related to myelodysplasia (MDS),". Br. J. Haematol. 89:831-837.
Rosenfeld, C. and Bedell, C., "Pilot study of recombinant human soluble tumor necrosis factor receptor (TNFR:Fc) in patients with low risk myelodysplastic syndromes," Leukemia Research, 2002, 26:721-724.
Rossetti et al., "Low-Dose Azacitidine for Relapse of MDS/AML After Unrelated Donor Peripheral Blood Stem Cell Transplantation," Blood, 2007, 110(11), Part II, 338B (American Society of Hematology, Annual Meeting, Dec. 8-11, 2007, Abstract #5034).
Samlowski et al., "Evaluation of gemcitabine in patients with recurrent or metastatic squamous cell carcinoma of the head and neck: a Southwest Oncology Group phase II study," Invest. New Drugs, 19(4):311-315 (2001).
Sampaio et al., "Prolonged treatment with recombinant interferon gamma induces erythema nodosum leprosum in lepromatous leprosy patients," J. Exp. Med. 175(6):1729-1737 (1992).
Sampaio et al., "Thalidomide selectively inhibits tumor necrosis factor alpha production by stimulated human monocytes," J. Exp. Med. 173(3):699-703 (1991).
Sanderson, Nature News, Mar. 16, 2009, available at http://www.nature.com/news/2009/090316/full/458269a.html.
Santini et al., "European Inter-Country Treatment Selection Differences Do Not Alter Overall Survival Benefit Shown with Azacitidine vs. Conventional Care Regimens in Higher-Risk Myelodysplastic Syndromes," Haematologica—The Hematology Journal, 2008, 93(Suppl. 1), p. 95 (13th Congress of the European Hematology Association, Jun. 12-15, 2008, Abstract #236).
Schey et al., "Phase I Study of an Immunomodulatory Thalidomide Analog, CC-4047, in Relapsed or Refractory Multiple Myeloma," J. Clin. Oncol. 22(16):3269-3276 (2004).
Schey et al., "Pomalidomide therapy for myeloma," Expert Opin. Invest. Drugs 20:691-700 (2011).
Schey et al., "Pomalidomide therapy for myeloma," Expert Opin. Invest. Drugs, 20(5): 691-700 (2011).
Schey et al., "A phase I study of an immunomodulatory thalidomide analogue (CC4047) in relapse/refractory multiple myeloma," International Society for Experimental Hematology, 31st Annual Meeting, Jul. 6-9, Montreal, Canada, 2002; Abstract #248.
Schey, "Thalidomide in the management of multiple myeloma," Hematology 7(5):291-299 (2002).
Schlossman et al., "Bone marrow transplatation in multiple myeloma," Curr. Opin. Oncol., 11(2):102-108 (1999).
Schrader et al., 1981, "The persisting (P) cell: histamine content, regulation by a T cell-derived factor, origin from a bone marrow precursor, and relationship to mast cells," Proc. Natl. Acad. Sci. USA 78(1):323-327.
Schuster et al., 1990, Blood 76(Supp. 1):318a.
Scott, et al., "Zebularine inhibits human acute myeloid leukemia cell growth in vitro in association with p15INK4B demethylation and reexpression," Experimental Hematology, 2007, 35(2):263-273.
Search Report in corresponding ARIPO Appl. No. AP/P/2006/003799 dated Mar. 3, 2009.
Sekeres et al., "Phase I Combination Trial of Lenalidomide and Azacitidine in Patients with Higher-Risk Myelodysplastic Syndromes," Journal of Clinical Oncology, 2010, 1-10.
Sekeres et al., "Preliminary Results from a Phase I Study of Revlimid® (Lenalidomide) in Combination with Vidaza® (Azacitidine) in Patients with Advanced Myelodysplastic Syndromes (MDS)," Blood, 2007, 110(11), Part I, 437A (American Society of Hematology, Annual Meeting, Dec. 8-11, 2007, Abstract #1458).
Sekeres, M., et al., "Final Results from a Phase I Combination Study of Lenalidomide and Azacitidine in Patients with Higher-Risk Myelodysplastic Syndromes (MDS)," Blood (ASH Annual Meeting Abstracts), 2008, 112: Abstract 221.
Seppa, "Thalidomide combats myeloma blood cancer," Science News 156:326 (1999).
Seppa, N., Thalidomide combats myeloma blood cancer, Science News, 156(21): 326 (1999).
Shetty, V., Allampallam, K., Hussaini, S., Townsend, W., Dutt, D., Mundle, S., Alvi, S., Reddy, P.L., Ashraf, H., Galili, N., Saberwal, G.S., Anthwal, S., Shaikh, M.W., Heidelberg, A., Lisak, L., Gezer, S., Venugopal, P., Raza, A., Effects of anti-cytokine agents on apoptosis, proliferation, monocyte/macrophage number, microvessel density and cytokines following two successive clinical trials in 57 patients with myelodysplastic syndromes (MDS). Abstract #4837. American Society of Hematology, Dec. 7-11, 2001.
Shinn et al., "Development of a computerized drug interaction database (MEDICOM) for use in a patient specific environment," Drug Inf. J., 17(3):205-210 (1983).
Shnider et al., Journal of Clinical Pharmacology, 1976, 205-12.
Siegel et al., "Long-term safety and efficacy of pomalidomide (POM) with or without low-dose dexamethasone (LoDEX) in relapsed and refractory multiple myeloma (RRMM) patients enrolled in the MM-002 phase II trial," J. Clin. Oncol. 31, 2013 (Abstract No. 8588).
Siegel, D. et al., "Long-term safety and efficacy of pomalidomide (POM) with or without low-dose dexamethasone (LoDEX) in relapsed and refractory multiple myeloma (RRMM) patients enrolled in the MM-002 phase II trial," J Clin Oncol 31, 2013 (suppl; abstr 8588).
Silverman et al., "Effects of Treatment with 5-Azacitidine on the In Vivo and In Vitro Hematopoiesis in Patients with Myelodysplastic Syndromes," Leukemia, 1993, 7 Suppl. 1, 21-29.
Silverman et al., "Rates of Infection and Bleeding are not Increased in Patients with Myelodysplastic Syndromes (MDS) Treated with Azacitidine Compared with Supportive Care," Blood, American Society of Hematology, 47th Annual Meeting, Dec. 10-13, 2005, Abstract #2525.
Silverman et al., "Response Rates in Patients with Acute Myeloid Leukemia (AML), Treated with Azacitidine, Using WHO and International Working Group (IWG) Criteria for Myelodysplastic Syndromes (MDS)," Blood, 2005, 106(11), Part I, 525A-526A (American Society of Hematology, Annual Meeting, Dec. 10-13, 2005, Abstract #1848).
Silverman et al., "Response Rates Using International Working Group (IWG) Criteria in Patients with Myelodysplastic Syndrome (MDS) Treated with Azacitidine," Blood, American Society of Hematology, 47th Annual Meeting, Dec. 10-13, 2005, Abstract #2526.
Silverman et al., Journal of Clinical Oncology, 2002, 20(10), 2429-40.
Silverman et al., Journal of Clinical Oncology, 2006, 24(24), 3895-3903.

(56) References Cited

OTHER PUBLICATIONS

Silverman, "Hypomethylating Agents in Myelodysplastic Syndromes Changing the Inevitable: The Value of Azacitidine as Maintenance Therapy, Effects on Transfusion and Combination with Other Agents," Leuk. Res., 2009, Suppl. 2, S18-21.
Silverman, L. et al., "Analysis of Survival, AML Transformation, and Transfusion Independence in Patients with High-Risk Myelodysplastic Syndromes (MDS) Receiving Azacitidine Determined Using a Prognostic Model. Session Type: Poster Session 727-II," American Society of Hematology, Dec. 10-13, 2005, Abstract #2523.
Silverman, L. et al., "Azacitidine Prolongs Survival and Time to AML Transformations in High-Risk Myelodysplastic Syndrome (MDS) Patients≥ 65 Years of Age," Blood, American Society of Hematology, 47th Annual Meeting, Dec. 10-13, 2005, Abstract #2524.
Silverman, L. et al., "The role of Azacitidine in the treatment of the Myelodysplasic Syndrome," Sixth International Symposium, Jun. 14-17, 2001, Abstract #0038.
Singhal et al., "Antitumor activity of thalidomide in refractory multiple myeloma," N. Engl. J. Med. 341(21):1565-1571 (1999).
Singhal et al., 1999, "Antitumor activity of thalidomide in refractory multiple myeloma," N. Engl. J. Med. 341(21):1565-1571.
Skikne et al., "A Phase I, Open-Label, Dose-Escalation Study to Evaluate the Safety, Pharmacokinetics, and Pharmacodynamics of Oral Azacitidine in Subjects with Myelodysplastic Syndromes (MDS) or Acute Myelogenous Leukemia (AML)," Journal of Clinical Oncology (May 20, 2008 Supplement), 2008 ASCO Annual Meeting Proceedings (Meeting Date: May 30-Jun. 3, 2008), Part I, 2008, 26(15S), poster # 7091.
Smith et al., "Studies on the relationship between the chemical structure and embryotoxic activity of thalidomide and related compounds," in A Symposium on Embiyopathic Activity of Drugs, J. & A. Churchill Ltd., 1965, Session 6, pp. 194-209.
Smith, R. et al., "Studies on the Relationship Between the Chemical Structure and Embryotoxic Activity of Thalidomide and Related Compounds," in A Symposium on Embryopathic Activity of Drugs, J. & A. Churchill Ltd., 1965, Session 6, pp. 194-209.
Sorbera, L. et al., "CC-5013. Treatment of Multiple Myeloma, Treatment of Melanoma, Treatment of Myelodysplastic Syndrome, Angiogenesis Inhibitor, TNF-$\alpha$ Production Inhibitor," Drugs of the Future, 2003, 28(5):425-431.
Soyka et al., "Prevalence of alcohol and drug abuse in schizophrenic inpatients," Eur. Arch. Psychiatry Clin. Neurosci., 242(6):362-372 (1993).
Srinivasan et al., American Journal of Clinical Oncology, 1982, 5, 411-15.
Stanley et al., 1976, "Factors regulating macrophage production and growth: identity of colony-stimulating factor and macrophage growth factor," J. Exp. Med. 143(3):631-647.
Steiner et al., "The assessment of refill compliance using pharmacy records: methods, validity, and applications," J. Clin. Epidemiol. 1997 50(1):105-116 (1997).
Stirling et al., "Thalidomide. A surprising recovery," J. Am. Pharm. Assoc., NS37(3):306-313 (1997).
Stirling, "Thalidomide: a novel template for anticancer drugs," Seminars Oncology, 28(6):602-606 (2001).
Stoltz et al., "Development of an Oral Dosage Form of Azacitidine: Overcoming Challenges in Chemistry, Formulation, and Bioavailability," Blood, 48th ASH Annual Meeting (Meeting Date: Dec. 9-12, 2006), 2006, 108, poster # 4850.
Strasser et al., "Thalidomide treatment in multiple myeloma," Blood Reviews, 2002, 16:207-215.
Strupp, C. et al., "Thalidomide for the treatment of patients with myelodysplastic syndromes," Leukemia, 2002, 16(1):1-6.
Szelényi et al., "Cyclophosphamide adriamycin and dexamethasone (CAD) is a highly effective therapy for patients with advanced multiple myeloma," Ann. Oncol., 12(1):105-108 (2001).
Tabbara et al., 1991, "Hematopoietic growth factors," Anticancer Res. 11(1):81-90.
Tan et al., "Clinical Trial of 5-Azacitidine (5-azaCR)," American Association for Cancer Research, 64th Annual Meeting, Abstract # 385, Apr. 11-13, 1973.
Tauro et al., 2002, "Functional disturbance of marrow stromal microenvironment in the myelodysplastic syndromes," Leukemia 16:785-790.
Teramura, M., Men-ekiyokusei Ryouhou, Current Therapy, 2000, 18(5):140-144 (in Japanese).
THALOMID™ (thalidomide) Capsules Revised Package Insert (Jul. 15, 1998).
Thatikonda et al., "Combination Methyltransferase and Histone Deacetylase Inhibition in Elderly Patients with Secondary Acute Myelogenous Leukemia," Blood, 2007, 110(11), Part II, 165B (American Society of Hematology, 49th Annual Meeting, Dec. 8-11, 2007, Abstract #4387).
The Comprehensive Guide to Banff, Understanding the VIIIth International Myeloma Workshop (Guide to Banff) was published by the International Myeloma Foundation in Jul. of 2001.
The Merck Manual, 1999, 17th ed., pp. 953-955.
Thomas, D.A. et al., "The revitalization of thalidomide," Annals of Oncology, Jul. 2001, 12(7):885-886.
Thomas, D.A., Aguayo, A., Estey, E., Albitar, M., O'Brien, S., Giles, F.J., Beran, M., Cortes, J., Zeldis, J., Keating, M.J., Barlogie, B., Kantarjian, H.M., Thalidomide as anti-angiogenesis therapy (rx) in refractory or relapsed leukemia. Abstract #2269, American Society of Hematology, Dec. 3-7, 1999.
Transcript of the FDA's "Forty-Seventh Meeting of the Dermatologic and Opthalmic Drugs Advisory Committee," Sep. 5, 1997 ("FDA Meeting Part 2").
Transcript of the Forty-Seventh Meeting of the Dermatologic and Ophthalmic Drugs Advisory Committee (Sep. 4, 1997).
Transcript of the Forty-Seventh Meeting of the Dermatologic and Ophthalmic Drugs Advisory Committee (Sep. 5, 1997).
Transcript of the Forty-Seventh Meeting of the Dermatologic and Ophthalmic Drugs Advisory Committee, at 137 (Sep. 4, 1997)).
Troetel, et al., Cancer Chemotherapy Reports, Part I, 1972, 56(3), 405-11.
Tseng et al., "Rediscovering thalidomide: a review of its mechanism of action, side effects, and potential uses," J. Am. Acad. Dermatol. 35(6):969-979 (1996).
Turk et al., 1996, "Binding of thalidomide to alphal-acid glycoprotein may be involved in its inhibition of tumor necrosis factor alpha production," PNAS USA 93:7552-7556.
U.S. Appl. No. 09/287,377, filed Apr. 7, 1999 (62 pages).
U.S. Appl. No. 60/372,348, filed Apr. 12, 2002 (85 pages).
U.S. Appl. No. 60/499,723, filed Sep. 4, 2003 (55 pages).
Vadas et al., 1983, "Activation of antibody-dependent cell-mediated cytotoxicity of human neutrophils and eosinophils by separate colony-stimulating factors," J. Immunol. 130(2):795-799.
Vadas et al., 1983, "Eosinophil activation by colony-stimulating factor in man: metabolic effects and analysis by flow cytometry," Blood 61(6):1232-1241.
Vanchieri, "Preparing for thalidomide's comeback," Ann. Intern. Med. 127(10):951-952 (1997).
Vasiliauskas et al., 1999, "An open-label pilot study of low-dose thalidomide in chronically active, steroid-dependent Crohn's disease," Gastroenterology 117(6):1278-1287.
Velez-Garcia et al., Cancer Treatment Reports, 1977, 61(9), 1675-77.
Vu et al., "Pomalidomie (POM) with Low-Dose Dexamethasone (LoDex) in Patients with Relapsed and Refractory Multiple Myeloma (RRMM): Outcomes Based on Prior Treatment Exposure," presented at 54th ASH Annual Meeting and Exposition, Atlanta, Georgia, Dec. 8-11, 2012,. Abstract #4070.
Vogelsang et al., "Thalidomide for the treatment of chronic graft-versus-host disease," N. Engl. J. Med. 326(16):1055-1058 (1992).
Walgren et al., "A Phase II Study of Intravenous Acacitidine Alone in Patients with Myelodysplastic Syndromes NCT00384956," Blood, 2007, 110(11), Part I, 435A (American Society of Hematology, Annual Meeting, Dec. 8-11, 2007, Abstract #1451).
Ward et al., "An Oral Dosage Formulation of Azacitidine: A Pilot Pharmacokinetic Study," Journal of Clinical Oncology (Jun. 20,

(56) References Cited

OTHER PUBLICATIONS

2007 Supplement), 2007 ASCO Annual Meeting Proceedings (Meeting Date: Jun. 1-5, 2007), Part I, 2007, 25(18S), poster # 7084.
Weber et al., "Thalidomide alone or with dexamethasone for multiple myeloma" [abstract]. Blood 94(suppl 1):604a. Abstract 2686 (1999).
Weber et al., "Thalidomide alone or with dexamethasone for multiple myeloma," Blood 94:604 (1999).
Weber et al., "Thalidomide with dexamethasone of resistant multiple myeloma," Blood 96:167 (2000).
Weber et al., "Thalidomide With Dexamethasone of Resistant Multiple Myeloma," Blood, 96 Supp. Nov. 2000, p. 167a Abstract 719.
Weisbart et al., 1986, "Biosynthetic human GM-CSF modulates the number and affinity of neutrophil f-Met-Leu-Phe receptors," J. Immunol. 137(11):3584-3587.
Welte et al., "Influence of socially desirable responding in a study of stress and substance abuse," Alcohol Clin. Exp. Res. 17(4):758-761 (1993).
Wijermans, P. et al., "Low-dose 5-aza-2'-deoxycytidine, a DNA Hypomethylating Agent, for the Treatment of High-Risk Myelodysplastic Syndrome: a Multicenter Phase II Study in Elderly Patients," Journal of Clinical Oncology, 2000, 18(5):956-962.
Wolff, ed., 1995, Burger's Medicinal Chemistry and Dmg Discovery, 5th ed., pp. 172-178, 949-982.
Yuen et al., "Phase I study of an antisense oligonucleotide to protein kinase C-α (ISIS 3521/CGP 64128A) in patients with cancer," Clin. Cancer Res. 5(11):3357-3363 (1999).
Zangari et al., "Increased risk of deep-vein thrombosis in patients with multiple myeloma receiving thalidomide chemotherapy," Blood, 98:1614 (2001).
Zangari et al., "Thrombogenic activity of doxombicin in myeloma patients receiving thalidomide: implications for therapy," Blood 100:1168-1171 (2002).
Zangari, M. Tricot, G., Zeldis, J., Eddlemon, P., Saghafifar, F., Barlogie, B., Results of Phase 1 Study of CC5013, for the Treatment of Multiple Myeloma (MM) Patients Who Replase After High Dose Chemotherapy (HDCT). Abstract #3226. American Society of Hematology, Dec. 7-11, 2001.
Zeldis et al., "S.T.E.P.S.: a comprehensive program for controlling and monitoring access to thalidomide," Clin. Ther. 21(2):31-330 (1999).
Ziemba, A. et al., "Development of oral demethlylating agents for the treatment of myelodysplastic syndromes," Nevada Cancer Institute, Las Vegas, NV and Shenzhen Graduate School of Peking University, Shenzhen, China.
Zorat, F. et al., "The clinical and biological effects of thalidomide in patients with myelodysplastic syndromes," *British Journal of Haematology*, 2001, 115:881-894.
Anderson et al., "Novel biologically based therapies for myeloma," VIII the International Myeloma Workshop, Banff, Alberta, Canada, May 4-8, 2001; Abstract #S27.
Richardson et al., "A phase I study of the safety and efficacy of CC5013 treatment for patients with relapsed multiple myeloma: Preliminary results," VIII the International Myeloma Workshop, Banff, Alberta, Canada, May 4-8, 2001; Abstract #P230.
Srkalovic et al. "Use of melphalan, thalidomide, and dexamethasone in treatment of refractory and relapsed multiple myeloma," Med. Oncol. 19:219-226 (2002).
Boudard et al., "Expression and Activity of Caspases 1 and 3 in Myelodysplastic Syndromes," *Leukemia*, 14:2045-2051 (2000).
Thomas et al., "Pilot studies of thalidomide in acute myelogenous leukemia, myelodysplastic syndromes, and myeloproliferative disorders," *Seminars in Hematology*, 37:26-34 (2000).

\* cited by examiner

MJERODYSPLASTIC SYNDROMES WITH A
COMBINATION THERAPY USING
LENALIDOMIDE AND AZACITIDINE

1. CROSS-REFERENCE TO RELATED APPLICATIONS

This application is a continuation of U.S. application Ser. No. 15/926,740, filed Mar. 20, 2018; which is a continuation of U.S. application Ser. No. 14/517,280, filed Oct. 17, 2014, now U.S. Pat. No. 9,925,207; which is a continuation of U.S. application Ser. No. 13/801,262, filed Mar. 13, 2013, now U.S. Pat. No. 9,056,120; which is a continuation application of U.S. application Ser. No. 12/777,765, filed May 11, 2010, now U.S. Pat. No. 8,404,716; which is a continuation-in-part of U.S. application Ser. No. 11/985,032, filed Nov. 12, 2007, now U.S. Pat. No. 7,863,297 which is a continuation of U.S. application Ser. No. 11/654,550, filed Jan. 16, 2007, now U.S. Pat. No. 7,393,863 which is a divisional of U.S. application Ser. No. 10/411,649 filed Apr. 11, 2003, now U.S. Pat. No. 7,189,740 which claims the benefit of U.S. Provisional Application No. 60/418,468, filed Oct. 15, 2002; the disclosure of each of which is incorporated by reference herein in its entirety.

2. FIELD

Provided herein are methods for the treatment of myelodysplastic syndromes ("MDS"), with an immunomodulatory compound, including, but not limited to, 3-(4-amino-1-oxo-1,3-dihydro-isoindol-2-yl)-piperidine-2,6-dione, which is also known as lenalidomide or Revlimid®, in combination with a cytidine analog, including, but not limited to, 5-azacytidine. Also included are methods for improving the overall survival of certain classes of patients having MDS. The invention also encompasses pharmaceutical compositions, dosing regimens, and the use of an immunomodulatory compound and 5-azacytidine in conjunction with transplantation therapy and/or other standard therapies for myelodysplastic syndromes.

3. BACKGROUND

3.1. Pathobiology of MDS

Myelodysplastic syndrome ("MDS") refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production. *The Merck Manual* 953 (17$^{th}$ ed. 1999) and List et al., 1990, *J. Clin. Oncol.* 8:1424.

The initial hematopoietic stem cell injury can be from causes such as, but not limited to, cytotoxic chemotherapy, radiation, virus, chemical exposure, and genetic predisposition. A clonal mutation predominates over bone marrow, suppressing healthy stem cells. In the early stages of MDS, the main cause of cytopenias is increased programmed cell death (apoptosis). As the disease progresses and converts into leukemia, gene mutation rarely occurs and a proliferation of leukemic cells overwhelms the healthy marrow. The disease course differs, with some cases behaving as an indolent disease and others behaving aggressively with a very short clinical course that converts into an acute form of leukemia.

About 15,000 people are diagnosed with MDS each year in the United States, and about 60,000 are living with the disease. MDS was first considered a distinct disease in 1976, and occurrence was estimated at 1500 new cases every year. At that time, only patients with less than five percent blasts were considered to have this disorder. Statistics from 1999 estimated 13,000 new cases per year and about 1000 cases per year in children, surpassing chronic lymphocytic leukemia as the most common form of leukemia in the western hemisphere. The perception that the incidence is increasing may be due to improvements in recognition and criteria for diagnosis. The disease is found worldwide.

An international group of hematologists, the French-American-British (FAB) Cooperative Group, classified MDS disorders into five subgroups, differentiating them from acute myeloid leukemia. *The Merck Manual* 954 (17$^{th}$ ed. 1999); Bennett J. M., et al., *Ann. Intern. Med.* 1985 October, 103(4): 620-5; and Besa E. C., *Med. Clin. North Am.* 1992 May, 76(3): 599-617. An underlying trilineage dysplastic change in the bone marrow cells of the patients is found in all subtypes.

There are two subgroups of refractory anemia characterized by five percent or less myeloblasts in bone marrow: (1) refractory anemia (RA) and; (2) RA with ringed sideroblasts (RARS), defined morphologically as having 15% erythroid cells with abnormal ringed sideroblasts, reflecting an abnormal iron accumulation in the mitochondria. Both have a prolonged clinical course and low incidence of progression to acute leukemia. Besa E. C., *Med. Clin. North Am.* 1992 May, 76(3): 599-617.

There are two subgroups of refractory anemias with greater than five percent myeloblasts: (1) RA with excess blasts (RAEB), defined as 6-20% myeloblasts, and (2) RAEB in transformation (RAEB-T), with 21-30% myeloblasts. The higher the percentage of myeloblasts, the shorter the clinical course and the closer the disease is to acute myelogenous leukemia. Patient transition from early to more advanced stages indicates that these subtypes are merely stages of disease rather than distinct entities. Elderly patients with MDS with trilineage dysplasia and greater than 30% myeloblasts who progress to acute leukemia are often considered to have a poor prognosis because their response rate to chemotherapy is lower than de novo acute myeloid leukemia patients. The World Health Organization (WHO) classification (1999) proposes to include all cases of RAEB-T, or patients with greater than 20% myeloblasts, in the category of acute leukemia because these patients have similar prognostic outcomes. However, their response to therapy is worse than the de novo or more typical acute myelogenous leukemia or acute nonlymphocytic leukemia (ANLL) patient. Id.

The fifth type of MDS, the most difficult to classify, is called chronic myelomonocytic leukemia (CMML). This subtype can have any percentage of myeloblasts but presents with a monocytosis of 1000/dL or more. It may be associated with splenomegaly. This subtype overlaps with a myeloproliferative disorder and may have an intermediate clinical course. It is differentiated from the classic chronic myelocytic leukemia (CML) that is characterized by a negative Ph chromosome. The recent WHO classification (1999) proposes that juvenile and proliferative CMML be listed separately from FAB under MDS/myeloproliferative disorder (MPD) with splenomegaly and greater than 13,000 total WBC. CMML is limited to monocytosis, less than 13,000/mm$^3$ total leukocytes, and requires trilineage dysplasia. Id. Harris N. L., et al., *J. Clin. Oncol.* 1999 December, 17(12): 3835-49. Finally, some other international organizations, including WHO, have suggested a sixth class of MDS patients, characterized by a del (5q) abnormality.

MDS is primarily a disease of elderly people, with the median onset in the seventh decade of life. The median age of these patients is 65 years, with ages ranging from the early third decade of life to as old as 80 years or older. The syndrome may occur in any age group, including the pediatric population. Patients who survive malignancy treatment with alkylating agents, with or without radiotherapy, have a high incidence of developing MDS or secondary acute leukemia. About 60-70% of patients do not have an obvious exposure or cause for MDS, and are classified as primary MDS patients.

The most common cases of MDS are primary, or idiopathic. However, a nonspecific history of exposure to indeterminable chemicals or radiation 10-15 years prior to onset of disease may be present in about 50% of patients. This relationship to pathogenesis remains unproved. Compounds such as, but not limited to, benzene, insecticides, weed killers, and fungicides are possible causes of MDS. Goldberg H., et al., *Cancer Res.* 1990 Nov. 1; 50(21): 6876-81. Secondary MDS describes development of MDS or acute leukemia after known exposures to chemotherapy drugs that can cause bone marrow damage. These drugs are associated with a high incidence of chromosomal abnormalities following exposure and at the time of MDS or acute leukemia diagnosis.

Further, MDS is associated with complications associated with severe cytopenias. Other complications are development of myelofibrosis, which can accelerate decline in blood counts and increase transfusion requirements. Transformation to acute leukemia accelerates the development of complications such as anemia, bleeding, and infections.

The International MDS Risk Analysis (IMRA) Workshop proposed an International Prognosis Scoring System (IPSS) to decrease imprecision in predicting survival and AML risk in MDS patients. The IPSS is based on the number of cytopenias, percentage of BM blasts, and type of cytogenetic abnormalities (Table 1). Greenberg et al., *Blood* 1997, 89:2079-88. The latter are categorized into good (normal, -Y, del (5q), del (20q)), intermediate, and poor subgroups (complex or chromosome 7 abnormalities).

TABLE 1

International Prognostic Scoring System for MDS

| Prognostic Variable | Score Value | | | | |
|---|---|---|---|---|---|
| | 0 | 0.5 | 1.0 | 1.5 | 2.0 |
| Bone marrow blasts (%) | <5 | 5-10 | — | 11-20 | 21-30 |
| Karyotype* | Good | Intermediate | Poor | | |
| Cytopenias | 0/1 | 2/3 | | | |

*Good, normal, del (5q), del (20q), -Y; Poor, complex (>3) or chromosome 7 abnormalities; Intermediate, +8, and other single or double abnormalities.

3.2. MDS Treatment

The current treatment of MDS is based on the stage and the mechanism of the disease that predominates the particular phase of the disease process. Bone marrow transplantation has been used in patients with poor prognosis or late-stage MDS. Epstein and Slease, 1985, *Surg. Ann.* 17:125. This type of therapy, however, is both painful for donor and recipient, because of the involvement of invasive procedures and can cause severe and even fatal complications to the recipient, particularly with allogeneic transplant and related Graft Versus Host Disease (GVHD) results. Therefore, the risk of GVHD restricts the use of bone marrow transplantation to patients with otherwise fatal diseases. Further, as most patients are elderly and only a few young MDS patients will have a matched donor, the use of bone marrow transplantation is limited.

An alternative approach to therapy for MDS is the use of hematopoietic growth factors or cytokines to stimulate blood cell development in a recipient. Dexter, 1987, *J. Cell Sci.* 88:1; Moore, 1991, *Annu. Rev. Immunol.* 9:159; and Besa E. C., *Med. Clin. North Am.* 1992 May, 76(3): 599-617. The process of blood cell formation, by which a small number of self-renewing stem cells give rise to lineage specific progenitor cells that subsequently undergo proliferation and differentiation to produce the mature circulating blood cells has been shown to be at least in part regulated by specific hormones. These hormones are collectively known as hematopoietic growth factors. Metcalf, 1985, *Science* 229:16; Dexter, 1987, *J. Cell Sci.* 88:1; Golde and Gasson, 1988, *Scientific American*, July:62; Tabbara and Robinson, 1991, *Anti-Cancer Res.* 11:81; Ogawa, 1989, *Environ. Health Presp.* 80:199; and Dexter, 1989, *Br. Med. Bull.* 45:337. The most well characterized growth factors include erythropoietin (EPO), granulocyte macrophage colony stimulating factor (GM-CSF), and granulocyte colony stimulating factor (G-CSF). Apart from inducing proliferation and differentiation of hematopoietic progenitor cells, such cytokines have also been shown to activate a number of functions of mature blood cells, including influencing the migration of mature hematopoietic cells. Stanley et al., 1976, *J. Exp. Med.* 143:631; Schrader et al., 1981, *Proc. Natl. Acad. Sci. U.S.A.* 78:323; Moore et al., 1980, *J. Immunol.* 125:1302; Kurland et al., 1979, *Proc. Natl. Acad. Sci. U.S.A.* 76:2326; Handman and Burgess, 1979, *J. Immunol.* 122:1134; Vadas et al., 1983, *Blood* 61:1232; Vadas et al., 1983, 1 *Immunol.* 130: 795; and Weibart et al., 1986, *J. Immunol.* 137:3584.

Unfortunately, hematopoietic growth factors have not proven effective in many clinical settings. Clinical trials of MDS patients treated with recombinant human GM-CSF and G-CSF have shown that while these cytokines can restore granulocytopoiesis in treated patients, their efficacy is restricted to the granulocyte or monocyte lineage with little or no improvement in hemoglobin or platelet counts. Schuster et al., 1990, *Blood* 76 (Suppl.1):318a. When such patients were treated with recombinant human EPO, a sustained improvement in hemoglobin or decrease in transfusion requirement was achieved in only less than 25% of patients. Besa et al., 1990, 76 (Suppl.1):133a; Hellstrom et al., 1990, 76 (Suppl.1):279a; Bowen et al., 1991, *Br. J. Haematol.* 77:419. Therefore, there remains a need for safe and effective methods of treating and managing MDS.

3.3. Thalidomide and Azacitidine

Thalidomide is a racemic compound sold under the tradename Thalomid® and chemically named α-(N-phthalimido) glutarimide or 2-(2,6-dioxo-3-piperidinyl)-1H-isoindole-1,3 (2H)-dione. Thalidomide was originally developed in the 1950's to treat morning sickness, but due to its teratogenic effects was withdrawn from use. Thalidomide has been approved in the United States for the acute treatment of the cutaneous manifestations of erythema nodosum leprosum in leprosy. *Physicians' Desk Reference*, 1154-1158 (56th ed., 2002). Because its administration to pregnant women can cause birth defects, the sale of thalidomide is strictly controlled. Id. Thalidomide has reportedly been studied in the treatment of other diseases, such as chronic graft-vs-host disease, rheumatoid arthritis, sarcoidosis, several inflammatory skin diseases, and inflammatory bowel disease. See generally, Koch, H. P., *Prog. Med. Chem.* 22:165-242

(1985). See also, Moller, D. R., et al., *J. Immunol.* 159: 5157-5161 (1997); Vasiliauskas, E. A., et al., *Gastroenterology* 117:1278-1287 (1999); Ehrenpreis, E. D., et al., *Gastroenterology* 117:1271-1277 (1999). It has further been alleged that thalidomide can be combined with other drugs to treat ischemia/repercussion associated with coronary and cerebral occlusion. See U.S. Pat. No. 5,643,915, which is incorporated herein by reference.

More recently, thalidomide was found to exert immunomodulatory and anti-inflammatory effects in a variety of disease states, cachexia in AIDS, and opportunic infections in AIDS. In studies to define the physiological targets of thalidomide, the drug was found to have a wide variety of biological activities exclusive of its sedative effect including neurotoxicity, teratogenicity, suppression of TNF-α production by monocytes/macrophages and the accompanying inflammatory toxicities associated with high levels of TNF-α, and inhibition of angiogenesis and neovascularization.

Additionally, beneficial effects have been observed in a variety of dermatological conditions, ulcerative colitis, Crohn's disease, Bechets's syndrome, systemic lupus erythematosis, aphthous ulcers, and lupus. The anti-angiogenic properties of thalidomide in in vivo models have been reported. D'Amato et al., *Thalidomide Is An Inhibitor Of Angiogenesis*, 1994, PNAS, USA 91:4082-4085.

One of the most therapeutically significant potential uses of thalidomide is in the treatment of cancer. The compound has been investigated in the treatment of various types of cancer, such as refractory multiple myeloma, brain, breast, colon, and prostate cancer, melanoma, mesothelioma, and renal cell carcinoma. See, e.g., Singhal, S., et al., *New England J. Med.* 341(21):1565-1571 (1999); and Marx, G. M., et al., *Proc. Am. Soc. Clin. Oncology* 18:454a (1999). Thalidomide reportedly can also be used to prevent the development of chronic cardiomyopathy in rats caused by doxorubicin. Costa, P. T., et al., *Blood* 92(10:suppl. 1):235b (1998). Other reports concerning the use of thalidomide in the treatment of specific cancers include its combination with carboplatin in the treatment of glioblastoma multiforme. McCann, J., *Drug Topics* 41-42 (Jun. 21, 1999). The use of thalidomide in combination with dexamethasone reportedly was effective in the treatment of patients suffering from multiple myeloma who also received, as supportive care, human granulocyte colony-stimulating factor (G-CSF), ciprofloxacin, and non-absorbable antifungal agents. Kropff, M. H., *Blood* 96(11 part 1):168a (2000); see also, Munshi, N. et al., *Blood* 94(10 part 1):578a (1999). Other chemotherapy combinations that comprise thalidomide are disclosed in International Application No. PCT/US01/15326 to R. Govindarjan and A. Zeitlan, and in International Application No. PCT/US01/15327 to J. B. Zeldis, et al.

In an effort to provide compounds that have greater therapeutic safety and efficacy than thalidomide, researchers have begun investigating a large number of other compounds, some of which are derivatives of thalidomide. See, e.g., Marriott, J. B., et al., *Expert Opin. Biol. Ther.* 1(4):1-8 (2001); G. W. Muller, et al., *Journal of Medicinal Chemistry* 39(17): 3238-3240 (1996); and G. W. Muller, et al., *Bioorganic & Medicinal Chemistry Letters* 8: 2669-2674 (1998). Examples include, but are not limited to, the substituted 2-(2,6-dioxopiperidin-3-yl) phthalimies and substituted 2-(2,6-dioxopiperidin-3-yl)-1-oxoisoindoles described in U.S. Pat. Nos. 6,281,230 and 6,316,471, both to G. W. Muller, et al.

A group of compounds selected for their capacity to potently inhibit TNF-α production by LPS stimulated PBMC has been investigated. L. G. Corral, et al., *Ann. Rheum. Dis.* 58:(Suppl I) 1107-1113 (1999). These compounds, which are referred to as IMiDs™ or Immunomodulatory Drugs, show not only potent inhibition of TNF-α but also marked inhibition of LPS induced monocyte IL1β and IL12 production. LPS induced IL6 is also inhibited by IMiDs™, albeit partially. These compounds are potent stimulators of LPS induced IL10, increasing IL10 levels by 200 to 300%. Id.

In addition, nucleoside analogs have been used clinically for the treatment of viral infections and proliferative disorders for decades. Most of the nucleoside analog drugs are classified as antimetabolites. After they enter cells, nucleoside analogs are successively phosphorylated to nucleoside 5'-monophosphates, 5'-diphosphates, and 5'-triphosphates. In most cases, nucleoside triphosphates are the chemical entities that inhibit DNA or RNA synthesis, either through a competitive inhibition of polymerases or through incorporation of modified nucleotides into DNA or RNA sequences. Nucleosides may act also as their diphosphates.

5-Azacytidine (also known as azacitidine and 4-amino-1-β-D-ribofuranosyl-1,3,5-triazin-2(1H)-one; Nation Service Center designation NSC-102816; CAS Registry Number 320-67-2) has undergone NCI-sponsored trials for the treatment of MDS. See, e.g., Kornblith et al., *J. Clin. Oncol.* 20(10): 2441-2452 (2002); Silverman et al., *J. Clin. Oncol.* 20(10): 2429-2440 (2002). 5-Azacytidine may be defined as having a molecular formula of $C_8H_{12}N_4O_5$, a relative molecular weight of 244.21 and a structure of:

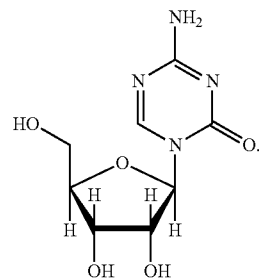

Azacitidine (also referred to as 5-azacytidine herein) is a nucleoside analog, more specifically a cytidine analog. 5-Azacytidine is an antagonist of its related natural nucleoside, cytidine. 5-Azacytidine, as well as decitabine, i.e., 5-aza-2'-deoxycytidine, are antagonists of decitabine's related natural nucleoside, deoxycytidine. The only structural difference between the analogs and their related natural nucleosides is the presence of nitrogen at position 5 of the cytosine ring in place of oxygen.

Other members of the class of deoxycytidine and cytidine analogs include arabinosylcytosine (Cytarabine), 2'-deoxy-2',2'-difluorocytidine (Gemcitabine), 5-aza-2'-deoxycytidine (Decitabine), 2(1H)-pyrimidine-riboside (Zebularine), 2',3'-dideoxy-5-fluoro-3'-thiacytidine (Emtriva), $N^4$-pentyloxycarbonyl-5'-deoxy-5-fluorocytidine (Capecitabine), 2'-cyclocytidine, arabinofuanosyl-5-azacytidine, dihydro-5-azacytidine, $N^4$-octadecyl-cytarabine, elaidic acid cytarabine, and cytosine 1-β-D-arabinofuranoside (ara-C).

There remains a need for more effective methods for treating MDS and its related disorders.

4. SUMMARY

Embodiments herein provide methods for the treatment of myelodysplastic syndromes (MDS) with a combination therapy using a therapeutically effective amount of a cytidine analog, including, but not limited to, 5-azacytidine, and a therapeutically effective amount of an immunomodulatory compound, including, but not limited to, 3-(4-amino-oxo-1,3-dihydro-isoindol-2-yl)-piperidine-2,6-dione (lenalidomide) or a pharmaceutically acceptable salt, solvate (e.g., hydrate) or stereoisomer thereof. Particular embodiments provide methods for treating patients with advanced MDS or higher risk MDS using the combination therapy. Particular embodiments provide methods for improving the overall survival of patients having MDS, e.g., higher risk MDS. Particular embodiments provide alternative dosing regimens for treating MDS. Particular embodiments provide methods for treating patients having MDS, using specific numbers of lenalidomide and azacitidine treatment cycles. Particular embodiments provide methods of treating patients who meet the WHO criteria for AML using lenalidomide and azacitidine. Particular embodiments provide using lenalidomide and azacytidine as maintenance therapy.

One embodiment encompasses the use of lenalidomide and azacitidine in combination with conventional therapies presently used to treat, prevent or manage MDS such as hematopoietic growth factors, cytokines, cancer chemotherapeutics, stem cell transplantation and other transplantations.

5. DETAILED DESCRIPTION

A first embodiment encompasses methods of treating or preventing MDS which comprise administering to a patient in need of such treatment or prevention a therapeutically or prophylactically effective amount of 3-(4-amino-oxo-1,3-dihydro-isoindol-2-yl)-piperidine-2,6-dione (lenalidomide), or a pharmaceutically acceptable salt, solvate, hydrate, stereoisomer, clathrate, or prodrug thereof, in combination with a therapeutically or prophylactically effective amount of a cytidine analog, particularly, 5-azacytidine. The embodiment encompasses the treatment, prevention or management of specific sub-types of MDS such as refractory anemia, refractory anemia with ringed sideroblasts, refractory anemia with excess blasts, refractory anemia with excess blasts in transformation and chronic myelomonocytic leukemia.

As used herein, the term "myelodysplastic syndromes" or "MDS" means hematopoietic stem cell disorders characterized by one or more of the following: ineffective blood cell production, progressive cytopenias, risk of progression to acute leukemia or cellular marrow with impaired morphology and maturation (dysmyelopoiesis). The term "myelodysplastic syndromes" or "MDS" unless otherwise noted includes: refractory anemia, refractory anemia with ringed sideroblasts, refractory anemia with excess blasts, refractory anemia with excess blasts in transformation and chronic myelomonocytic leukemia.

Another embodiment encompasses methods of managing MDS which comprises administering to a patient in need of such management a prophylactically effective amount of lenalidomide, or a pharmaceutically acceptable salt, solvate, hydrate, stereoisomer, clathrate, or prodrug thereof, in combination with a therapeutically or prophylactically effective amount of 5-azacytidine.

Another embodiment encompasses a kit comprising: a pharmaceutical composition comprising (1) lenalidomide, or a pharmaceutically acceptable salt, solvate, hydrate, stereoisomer, clathrate, or prodrug thereof, and (2) 5-azacytidine, and/or (3) instructions for use. The invention further encompasses kits comprising single unit dosage forms.

One embodiment encompasses a method of treating, preventing and/or managing MDS, which comprises administering to a patient in need of such treatment, prevention and/or management therapeutically or prophylactically effective amounts of 5-azacytidine and lenalidomide, or a pharmaceutically acceptable salt, solvate, hydrate, stereoisomer, clathrate, or prodrug thereof, and a therapeutically or prophylactically effective amount of an additional active agent.

The additional active agent is preferably a hematopoietic growth factor, a cytokine, an anti-cancer agent, an antibiotic, an anti-fungal, an anti-inflammatory, an immunosuppressive agent such as a cyclosporin, conventional therapy for MDS, or other chemotherapeutic agent found for example in the Physician's Desk Reference. Preferred anti-cancer or cancer chemotherapeutics are apoptosis inducing agents, topoisomerase inhibitors, anti-angiogenesis compounds, microtubule stabilizing agents, alkylating agents and other known conventional cancer chemotherapy. Most preferred additional active agents are those capable of affecting or improving blood production. The active agents can be large molecules (e.g., proteins) or small molecules (e.g., synthetic inorganic, organometallic, or organic molecules). The examples of specific additional active agent include, but are not limited to, gemtuzumab ozogamicin, etanercept (Enbrel®), imatinib (Glivec®), anti-TNF-α antibodies, infliximab (Remicade®), G-CSF, GM-CSF, EPO, topotecan, irinotecan, pentoxifylline, ciprofloxacin, dexamethasone, IL2, IL8, IL18, Ara-C, vinorelbine, vinblastine, isotretinoin, and 13-cis-retinoic acid. This invention also encompasses the use of native, naturally occurring, and recombinant proteins. The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., J. Immunol. Methods 248:91-101 (2001). Vaccines that cause the secretion of proteins disclosed herein as well as pharmacologically active mutants, derivatives, and fusion thereof are also encompassed by the invention.

Without being limited by theory, it is believed that certain immunomodulatory compounds and proteins can act in complementary or synergistic ways in the treatment or management of MDS. It is also believed that certain proteins may reduce or eliminate particular adverse effects associated with some immunomodulatory compounds, thereby allowing the administration of larger amounts of an immunomodulatory compound to patients and/or increasing patient compliance. It is further believed that some immunomodulatory compounds may reduce or eliminate particular adverse effects associated with some protein-based MDS therapies, thereby allowing the administration of larger amounts of protein to patients and/or increasing patient compliance.

Another embodiment of the invention encompasses a method of reversing, reducing or avoiding an adverse effect associated with the administration of a chemotherapeutics or therapeutics used to treat cancer or MDS in a patient suffering from MDS, which comprises administering to a patient in need thereof therapeutically or prophylactically effective amounts of azacitidine and lenalidomide, or a pharmaceutically acceptable salt, solvate, hydrate, stereoisomer, clathrate, or prodrug thereof.

As inevitable leukemic transformation develops in certain stages of MDS, transplantation of peripheral blood stem cells, hematopoietic stem cell preparation or bone marrow may be necessary. It is believed that the combined use of an immunomodulatory compound and transplantation of stem cells in a patient suffering from MDS provides a unique and unexpected synergism. In particular, without being limited by theory, it is believed that an immunomodulatory compound exhibits immunomodulatory activity that may provide additive or synergistic effects when given concurrently with transplantation therapy. Immunomodulatory compounds can work in combination with transplantation therapy reducing complications associated with the invasive procedure of transplantation and risk of related Graft Versus Host Disease (GVHD). Therefore, this invention encompasses a method of treating, preventing and/or managing MDS, which comprises administering to a patient (e.g., a human) azacitidine and lenalidomide, or a pharmaceutically acceptable salt, solvate, hydrate, stereoisomer, clathrate, or prodrug thereof, before, during, or after transplantation therapy.

The invention also encompasses pharmaceutical compositions, single unit dosage forms, and kits which comprise azacitidine and lenalidomide, or a pharmaceutically acceptable salt, solvate, hydrate, stereoisomer, clathrate, or prodrug thereof, an additional active ingredient, and/or blood or cells for transplantation therapy. For example, the kit may contain one or more compounds of the invention, stem cells for transplantation and an immunosuppressive agent, antibiotic or other drug, each of which is to be used to treat the MDS patient.

5.1. Immunomodulatory Compounds

Compounds used in the invention include immunomodulatory compounds that are racemic, stereomerically enriched or stereomerically pure, and pharmaceutically acceptable salts, solvates, hydrates, stereoisomers, clathrates, and prodrugs thereof. Preferred compounds used in the invention are small organic molecules having a molecular weight less than about 1000 g/mol, and are not proteins, peptides, oligonucleotides, oligosaccharides or other macromolecules.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein and unless otherwise indicated, the term "immunomodulatory compounds" or "IMiDs™" (Celgene Corporation) used herein encompasses small organic molecules that markedly inhibit TNF-α, LPS induced monocyte IL1β and IL12, and partially inhibit IL6 production. Specific immunomodulatory compounds of the invention are discussed below.

TNF-α is an inflammatory cytokine produced by macrophages and monocytes during acute inflammation. TNF-α is responsible for a diverse range of signaling events within cells. TNF-α may play a pathological role in cancer. Without being limited by particular theory, one of the biological effects exerted by the immunomodulatory compounds of the invention is the reduction of synthesis of TNF-α. Immunomodulatory compounds of the invention enhance the degradation of TNF-α mRNA.

Further, without being limited by particular theory, immunomodulatory compounds used in the invention may also be potent co-stimulators of T cells and increase cell proliferation dramatically in a dose dependent manner. Immunomodulatory compounds of the invention may also have a greater co-stimulatory effect on the CD8+ T cell subset than on the CD4+ T cell subset. In addition, the compounds preferably have anti-inflammatory properties, and efficiently co-stimulate T cells.

Specific examples of immunomodulatory compounds of the invention, include, but are not limited to, cyano and carboxy derivatives of substituted styrenes such as those disclosed in U.S. Pat. No. 5,929,117; 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. No. 5,874,448; the tetra substituted 2-(2,6-dioxopiperdin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide and EM-12), including, but not limited to, those disclosed in U.S. Pat. No. 5,635,517; and a class of non-polypeptide cyclic amides disclosed in U.S. Pat. Nos. 5,698,579 and 5,877,200; analogs and derivatives of thalidomide, including hydrolysis products, metabolites, derivatives and precursors of thalidomide, such as those described in U.S. Pat. Nos. 5,593,990, 5,629,327, and 6,071,948 to D'Amato; aminothalidomide, as well as analogs, hydrolysis products, metabolites, derivatives and precursors of aminothalidomide, and substituted 2-(2,6-dioxopiperidin-3-yl) phthalimides and substituted 2-(2,6-dioxopiperidin-3-yl)-1-oxoisoindoles such as those described in U.S. Pat. Nos. 6,281,230 and 6,316,471; isoindole-imide compounds such as those described in U.S. patent application Ser. No. 09/972,487 filed on Oct. 5, 2001, U.S. patent application Ser. No. 10/032,286 filed on Dec. 21, 2001, and International Application No. PCT/US01/50401 (International Publication No. WO 02/059106). The entireties of each of the patents identified herein are incorporated herein by reference. Immunomodulatory compounds of the invention do not include thalidomide.

Other specific immunomodulatory compounds of the invention include, but are not limited to, 1-oxo-and 1,3 dioxo-2-(2,6-dioxopiperidin-3-yl) isoindolines substituted with amino in the benzo ring as described in U.S. Pat. No. 5,635,517 which is incorporated herein. These compounds have the structure I:

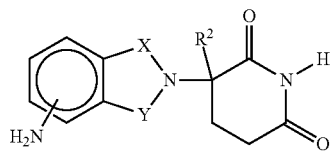

in which one of X and Y is C=O, the other of X and Y is C=O or CH$_2$, and R$^2$ is hydrogen or lower alkyl, in particular methyl. Specific immunomodulatory compounds include, but are not limited to:

1-oxo-2-(2,6-dioxopiperidin-3-yl)-4-aminoisoindoline;

1-oxo-2-(2,6-dioxopiperidin-3-yl)-5-aminoisoindoline;

1-oxo-2-(2,6-dioxopiperidin-3-yl)-6-aminoisoindoline;

1-oxo-2-(2,6-dioxopiperidin-3-yl)-7-aminoisoindoline;

1,3-dioxo-2-(2,6-dioxopiperidin-3-yl)-4-aminoisoindoline; and 1,3-dioxo-2-(2,6-dioxopiperidin-3-yl)-5-aminoisoindoline.

Other specific immunomodulatory compounds of the invention belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein. Compounds representative of this class are of the formulas:

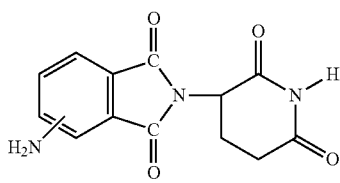

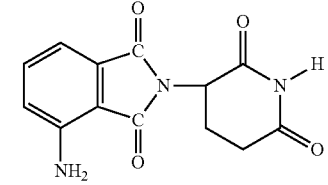

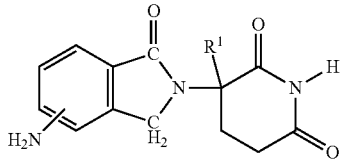

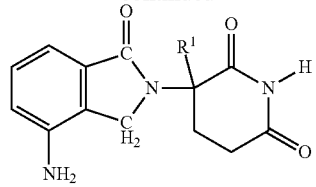

wherein R$^1$ is hydrogen or methyl. In a separate embodiment, the invention encompasses the use of enantiomerically pure forms (e.g. optically pure (R) or (S) enantiomers) of these compounds.

Still other specific immunomodulatory compounds of the invention belong to a class of isoindole-imides disclosed in U.S. patent application Ser. Nos. 10/032,286 and 09/972,487, and International Application No. PCT/US01/50401 (International Publication No. WO 02/059106), each of which are incorporated herein by reference. Representative compounds are of formula II:

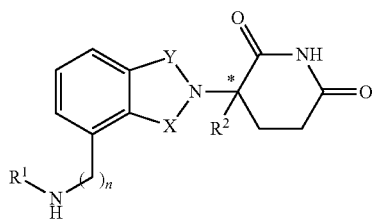

and pharmaceutically acceptable salts, hydrates, solvates, clathrates, enantiomers, diastereomers, racemates, and mixtures of stereoisomers thereof, wherein:

one of X and Y is C=O and the other is CH$_2$ or C=O;

R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(O)NHR$^3$, C(S)NHR$^3$, C(O)NR$^3$R$^{3'}$, C(S)NR$^3$R$^{3'}$ or (C$_1$-C$_8$)alkyl-O(CO)R$^5$;

R$^2$ is H, F, benzyl, (C$_1$-C$_8$)alkyl, (C$_2$-C$_8$)alkenyl, or (C$_2$-C$_8$)alkynyl;

R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$;

R$^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl-(C$_1$-C$_6$)heterocycloalkyl, or (C$_0$-C$_4$)alkyl-(C$_2$-C$_5$)heteroaryl;

R$^5$ is (C$_1$-C$_8$)alkyl, (C$_2$-C$_8$)alkenyl, (C$_2$-C$_8$)alkynyl, benzyl, aryl, or (C$_2$-C$_5$)heteroaryl;

each occurrence of R$^6$ is independently H, (C$_1$-C$_8$)alkyl, (C$_2$-C$_8$)alkenyl, (C$_2$-C$_8$)alkynyl, benzyl, aryl, (C$_2$-C$_5$)heteroaryl, or (C$_0$-C$_8$)alkyl-C(O)O—R$^5$ or the R$^6$ groups can join to form a heterocycloalkyl group;

n is 0 or 1; and

* represents a chiral-carbon center.

In specific compounds of formula II, when n is 0 then R$^1$ is (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(S)NHR$^3$, or (C$_1$-C$_8$)alkyl-O(CO)R$^5$;

$R^2$ is H or $(C_1-C_8)$alkyl; and $R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_5-C_8)$alkyl-N$(R^6)_2$, $(C_0-C_8)$alkyl-NH—C(O)O—$R^5$; $(C_1-C_8)$alkyl-O$R^5$, $(C_1-C_8)$alkyl-C(O)O$R^5$, $(C_1-C_8)$alkyl-O(CO)$R^5$, or C(O)O$R^5$, and the other variables have the same definitions.

In other specific compounds of formula II, $R^2$ is H or $(C_1-C_4)$alkyl.

In other specific compounds of formula II, $R^1$ is $(C_1-C_8)$ alkyl or benzyl.

In other specific compounds of formula II, $R^1$ is H, $(C_1-C_8)$alkyl, benzyl, $CH_2OCH_3$, $CH_2CH_2OCH_3$, or

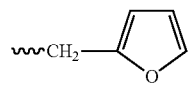

In another embodiment of the compounds of formula II, $R^1$ is

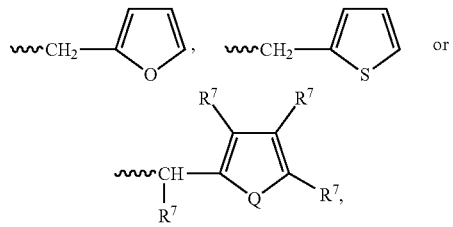

wherein Q is O or S, and each occurrence of $R^7$ is independently H, $(C_1-C_8)$alkyl, benzyl, $CH_2OCH_3$, or $CH_2CH_2OCH_3$.

In other specific compounds of formula II, $R^1$ is C(O)$R^3$.

In other specific compounds of formula II, $R^3$ is $(C_0-C_4)$ alkyl-$(C_2-C_5)$heteroaryl, $(C_1-C_8)$alkyl, aryl, or $(C_0-C_4)$alkyl-O$R^5$.

In other specific compounds of formula II, heteroaryl is pyridyl, furyl, or thienyl.

In other specific compounds of formula II, $R^1$ is C(O) O$R^4$.

In other specific compounds of formula II, the H of C(O)NHC(O) can be replaced with $(C_1-C_4)$alkyl, aryl, or benzyl.

Still other specific immunomodulatory compounds of the invention belong to a class of isoindole-imides disclosed in U.S. patent application Ser. No. 09/781,179, International Publication No. WO 98/54170, and U.S. Pat. No. 6,395,754, each of which are incorporated herein by reference. Representative compounds are of formula III:

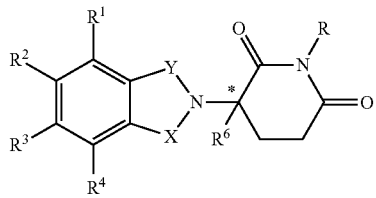

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O; R is H or $CH_2OCOR'$;

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —NH$R^5$ and the remaining of $R^1$, $R^2$, $R^3$, or $R^4$ are hydrogen;

$R^5$ is hydrogen or alkyl of 1 to 8 carbons;

$R^6$ hydrogen, alkyl of 1 to 8 carbon atoms, benzo, chloro, or fluoro; and

* represents a chiral-carbon center.

The most preferred immunomodulatory compounds of the invention are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635,517, incorporated herein by reference). The compounds are available from Celgene Corporation, Summit, N.J. 4-(Amino)-2-(2,6-dioxo(3-piperidyl))-isoindoline-1,3-dione (pomalidomide) has the following chemical structure:

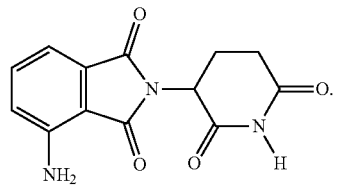

3-(4 Amino-1-oxo-1,3-dihydro-isoindol-2-yl)-piperidine-2,6-dione (lenalidomide) has the following chemical structure:

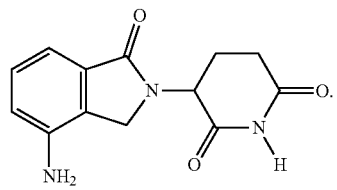 [SMILES: Nc1cccc2c1CN(C1CCC(=O)NC1=O)C2=O]

The compounds of the invention can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of immunomodulatory compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the invention that comprise —NO, —NO$_2$, —ONO, or —ONO$_2$ moieties. Prodrugs can typically be prepared using well known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elsevier, New York 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkyl amines, heterocyclic and heteroaromatic amines, and polyether amines.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.2. Additional Active Agents

One or more additional active ingredients can be used in the methods and compositions of the invention together with azacitidine and an immunomodulatory compound of the invention. In a preferred embodiment, the additional active agents are capable of affecting or improving the process of blood cell production. Specific additional active agents also stimulate the division and differentiation of committed erythroid progenitors in cells in vitro or in vivo.

Additional active agents can be large molecules (e.g., proteins) or small molecules (e.g., synthetic inorganic, organometallic, or organic molecules). The additional active agents include but are not limited to hematopoietic growth factors, cytokines, anti-cancer agents, antibiotics, proteasome inhibitors, immunosuppressive agents and other therapeutics discussed herein. Particular agents include, but are not limited to, G-CSF, GM-CSF, EPO, dexamethasone, topotecan, pentoxifylline, irinotecan, ciprofloxacin, vinorelbine, IL2, IL8, IL18, Ara-C, isotretinoin, 13-cis-retinoic acid, 12-O-tetradecanoylphorbol-13-acetate (TPA), 5-AZA2'-deoyxcytidine, 9-nitrocamp-tothecin, transretinoic acid, amifostine, amphotericin B and liposomal amphotericin B, anti-CD-20 monoclonal antibody, anti-thymocyle globulin (ATG), arsenic trioxide, azacytidine, bevacizumab, bismuth monoclonal antibody, bryostatin, busulfan, caspofungin acetate, celocoxib, cladribine, cyclophosphamide, cyclosporine, cytarabine, cytosine, daunorubicin, depsipeptide, etoposide, farresy transferase inhibitor, flavopiridol, Flt3 ligand, fludarabine, gentuzumab ozogomicin (mylotarg), etanercept (Enbrel®), imatinib (Glivec®), anti-TNF-α antibodies, infliximab (Remicade®), humanized monoclonal anti-VEGF antibody, idarubicine, leucovorin, melphalan, mitoxantrone, monoclonal antibody ABX-CBL, monoclonal antibody CD52, mycophenolate mofetil, oblimersen, omega-3 fatty acids, pentostatin, phenylbutyrate, PR1 leukemia peptide vaccine, montanide, proteasome inhibitor, sodium phenylbutyrate, sodium salicylate, temozolomide, thymoglobulin, troxatyl, tumor necrosis factor receptor IgG chimera, Yttrium Y 90 humanized monoclonal antibody M195. In a specific embodiment of the invention, an immunomodulatory compound of the invention is used in combination with pentoxifylline, ciprofloxacin, and/or dexamethasone.

This invention also encompasses the use of native, naturally occurring, and recombinant proteins. The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Recombinant and mutated forms of G-CSF can be prepared as described in U.S. Pat. Nos. 4,810,643; 4,999,291; 5,528,823; and 5,580,755; all of which are incorporated herein by reference. Recombinant and mutated forms of GM-CSF can be prepared as described in U.S. Pat. Nos. 5,391,485; 5,393,870; and 5,229,496; all of which are incorporated herein by reference. In fact, recombinant forms of G-CSF and GM-CSF are currently sold in the United States for the treatment of symptoms associated with specific chemotherapies. A recombinant form of G-CSF known as filgrastim is sold in the United States under the trade name NEUPOGEN®. NEUPOGEN® is known to stimulate division and maturation of granulocytes, mostly neutrophils, in MDS patients and to enhance erythroid response in combination with EPO. *Physicians' Desk Reference*, 587-592 (56$^{th}$ ed., 2002). A recombinant form of GM-CSF known as sargramostim is also sold in the United States under the trade name LEUKINE®. LEUKINE® is known to stimulate division and maturation of earlier myeloid and macrophage precursor cells and has been reported to increase granulocytes. *Physicians' Desk Reference*, 1755-1760 (56$^{th}$ ed., 2002). A recombinant form of EPO known as epoetin alfa is sold in the United States under the trade name EPOGEN®. EPOGEN® is used to stimulate red cell production by stimulating division and maturation of committed red cell precursor cells. EPOGEN® has been reported to be effective in 20-26% of MDS patient when administered by itself and in as many as 48% of patients when combined with G-CSF or GM-CSF. *Physicians' Desk Reference*, 582-587 (56$^{th}$ ed., 2002).

A growth-factor or cytokine such as G-CSF, GM-CSF and EPO can also be administered in the form of a vaccine. For example, vaccines that secrete, or cause the secretion of, cytokines such as G-CSF and GM-CSF can be used in the methods, pharmaceutical compositions, and kits of the invention. See, e.g., Emens, L. A., et al., *Curr. Opinion Mol. Ther.* 3(1):77-84 (2001).

Other compounds that can be administered or used in combination with an immunomodulatory compound of the invention include those disclosed in U.S. provisional patent application No. 60/380,842, filed May 17, 2002, and U.S. provisional patent application No. 60/380,843, filed May 17, 2002, both of which are incorporated herein by reference.

5.3. Methods of Treatment and Management

Methods of this invention encompass methods of preventing, treating and/or managing various types of MDS. As used herein, unless otherwise specified, the term "preventing" includes but is not limited to, inhibition or the averting of symptoms associated with MDS. The symptoms associated with MDS include, but are not limited to, anemia, thrombocytopenia, neutropenia, cytopenia, bicytopenia (two deficient cell lines), and pancytopenia (three deficient cell lines). As used herein, unless otherwise specified, the term "treating" refers to the administration of a composition after the onset of symptoms of MDS, whereas "preventing" refers to the administration prior to the onset of symptoms, particularly to patients at risk of MDS. As used herein and unless otherwise indicated, the term "managing" encompasses preventing the recurrence of MDS in a patient who had suffered from MDS, lengthening the time a patient who had suffered from MIDS remains in remission, and/or preventing the occurrence of MDS in patients at risk of suffering from MDS.

The invention encompasses methods of treating or preventing patients with primary and secondary MDS. It further encompasses methods treating patients who have been previously treated for MDS, as well as those who have not previously been treated for MDS. Because patients with MDS have heterogenous clinical manifestations and varying clinical outcomes, it has become apparent that staging the patients according to their prognosis and approaching therapy depending on the severity and stage is necessary. Indeed, the methods and compositions of this invention can be used in various stages of treatments for patients with one or more types of MDS including, but not limited to, refractory anemia (RA), RA with ringed sideroblasts (RARS), RA with excess blasts (RAEB), RAEB in transformation (RAEB-T), or chronic myelomonocytic leukemia (CMML). The invention also contemplates treating patients diagnosed using the IPSS for MDS discussed above. Greenberg et al., *Blood* 1997 (89):2079-88.

Methods encompassed by this invention comprise administering azacitidine and an immunomodulatory compound of the invention, or a pharmaceutically acceptable salt, solvate, hydrate, stereoisomer, clathrate, or prodrug thereof to a patient (e.g., a human) suffering, or likely to suffer, from MDS. Specific patient populations include the elderly, i.e., ages 60 and above as well as those over 35 years of age. Patients with familial history of MDS or leukemia are also preferred candidates for preventive regimens.

In one embodiment of the invention, an immunomodulatory compound of the invention is administered orally and in a single or divided daily doses in an amount of from about 0.10 to about 150 mg/day. In a particular embodiment, 4-(amino)-2-(2,6-dioxo(3-piperidyl))-isoindoline-1,3-dione (pomalidomide) is administered in an amount of from about 0.1 to about 10 mg per day, or alternatively every other day. 3-(4-Amino-1-oxo-1,3-dihydro-isoindol-2-yl)-piperidine-2,6-dione (lenalidomide) can be preferably administered in an amount of from about 5 to 25 mg per day, or alternatively every other day.

In one embodiment of the invention, azacitidine is administered according to one of three alternative dosing schedules, administered in 28-day cycles:

1) AZA 5-2-2: azacitidine 75 mg/m$^2$/day SC×5 days, followed by 2 days of no treatment, followed by azacitidine 75 mg/m$^2$/day SC×2 days;
2) AZA 5-2-5: azacitidine 50 mg/m$^2$/day SC×5 days, followed by 2 days of no treatment, followed by azacitidine 50 mg/m$^2$/day SC×5 days; and
3) AZA 5: azacitidine 75 mg/m$^2$/day SC×5 days.

After at least 2 cycles, azacitidine dose can be increased if the patient is not responding, defined as treatment failure or disease progression according to IWG 2000 criteria for MDS (≥50% increase in blasts, ≥50% decrease from maximum response levels in granulocytes or platelets, hemoglobin reduction ≥2 g/dL, or transfusion independence). Conversely, the dose can be decreased based on hematological recovery and adverse events.

5.3.1 Combination Therapy with Additional Active Agent

Particular methods of the invention comprise comprises administering 1) an immunomodulatory compound of the invention, or a pharmaceutically acceptable salt, solvate, hydrate, stereoisomer, clathrate, or prodrug thereof, 2) azacitidine and 3) an additional active agent or active ingredient. Examples of immunomodulatory compounds of the invention are disclosed herein (see, e.g., section 5.1); and examples of the additional active agents are also disclosed herein (see, e.g., section 5.2).

Administration of the immunomodulatory compounds, azacitidine and the additional active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for an immunomodulatory compound is oral. A preferred route of administration for azacitidine is subcutaneous, intravenous or oral. Preferred routes of administration for the additional active agents or ingredients of the invention are known to those of ordinary skill in the art. See, e.g., *Physicians' Desk Reference*.

In one embodiment, the additional active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the additional active agent will depend on the specific agent used, the type of MDS being treated or managed, the severity and stage of MDS, and the amount(s) of immunomodulatory compounds of the invention and any optional additional active agents concurrently administered to the patient. In a particular embodiment, the additional active agent is gemtuzumab ozogamicin, etanercept, GM-CSF, G-CSF, EPO, transretinoic acid, dexamethasone, topotecan, pentoxifylline, ciprofloxacin, dexamethasone, IL2, IL8, IL18, Ara-C, vinorelbine, or a combination thereof. GM-CSF is administered in an amount of from about 60 to about 500 mcg/m$^2$ intravenously over 2 hours, or from about 5 to about 12 mcg/m$^2$/day subcutaneously. G-CSF is administered subcutaneously in an amount of about 1 mcg/kg/day initially and can be adjusted depending on rise of total granulocyte counts. The maintenance dose is 300 (in smaller patients) or 480 mcg subcutaneously. EPO is administered subcutaneously in an amount of 10,000 Unit 3 times per week.

5.3.2 Use with Transplantation Therapy

In still another embodiment, this invention encompasses a method of treating, preventing and/or managing MDS, which comprises administering azacitidine and the immunomodulatory compound of the invention, or a pharmaceutically acceptable salt, solvate, hydrate, stereoisomer, clathrate, or prodrug thereof, in conjunction with transplantation therapy. As discussed elsewhere herein, the treatment of MDS is based on the stages and mechanism of the disease. As inevitable leukemic transformation develops in certain stages of MDS, transplantation of peripheral blood stem cells, hematopoietic stem cell preparation or bone marrow may be necessary. The combined use of azacitidine, the immunomodulatory compound of the invention and transplantation therapy provides a unique and unexpected synergism. In particular, an immunomodulatory compound of the invention exhibits immunomodulatory activity that may provide additive or synergistic effects when given concurrently with transplantation therapy in patients with MDS. An immunomodulatory compound of the invention can work in combination with transplantation therapy reducing complications associated with the invasive procedure of transplantation and risk of related Graft Versus Host Disease (GVHD). This invention encompasses a method of treating, preventing and/or managing MDS which comprises administering to a patient (e.g., a human) azacitidine and an immunomodulatory compound of the invention, or a pharmaceutically acceptable salt, solvate, hydrate, stereoisomer, clathrate, or prodrug thereof, before, during, or after the transplantation of umbilical cord blood, placental blood, peripheral blood stem cell, hematopoietic stem cell preparation or bone marrow. Examples of stem cells suitable for use in the methods of the invention are disclosed in U.S. provisional patent application No. 60/372,348, filed Apr. 12, 2002 by R. Hariri et al., the entirety of which is incorporated herein by reference.

5.3.3 Cycling Therapy

In a preferred embodiments, the therapeutic agents of the invention are cyclically administered to a patient. Cycling therapy involves the administrations of the first agent and the second agent for periods of time, followed by rest for periods of time, and repeating the sequential administrations. Cycling therapy can reduce the development of resistance to the therapies, avoid or reduce the side effects of the therapies, and/or improves the efficacy of the treatment.

In a particular embodiment, one cycle can comprise the administration of a therapeutic agent for three (3) weeks followed by one (1) week of rest in a 28-days cycle. The number of cycles administered is from about 1 to about 12 cycles. 3-(4-Amino-1-oxo-1,3-dihydro-isoindol-2-yl)-piperidin-2,6-dione (lenalidomide) is orally administered to patients with MDS in an amount of about 5-25 mg per day for 21 days followed by seven days rest on a 28 day cycle. In a particular embodiment, lenalidomide is orally administered to patients with MDS in an amount of about 10 mg per day for 21 days followed by seven days rest on a 28 day cycle.

In a particular embodiment, the patient also receive 5-azacytidine at a dose of about 25-75 mg/m$^2$/d subcutaneously (SC) or intravenously (IV) for days 1-7 followed by twenty-one days rest on a 28 day cycle. In another particular embodiment, patient receive 5-azacytidine at a dose of about 25-75 mg/m$^2$/d subcutaneously (SC) or intravenously (IV) for days 1-5 followed by twenty-three days rest on a 28 day cycle. In another particular embodiment, patient receive oral 5-azacytidine at a dose of about 120 mg/d for days 1-7 followed by twenty-one days rest on a 28 day cycle.

In one embodiment, up to 9 or more 28-day cycles are administered. Other methods for providing an effective amount of a cytidine analog are disclosed in, for example, "Colon-Targeted Oral Formulations of Cytidine Analogs", U.S. Ser. No. 11/849,958, which is incorporated by reference herein in its entirety.

5.4. Pharmaceutical Compositions and Single Unit Dosage Forms

Pharmaceutical compositions can be used in the preparation of individual, single unit dosage forms. Pharmaceutical compositions and dosage forms of the invention comprise an immunomodulatory compound of the invention, or a pharmaceutically acceptable salt, solvate, hydrate, stereoisomer, clathrate, or prodrug thereof. Pharmaceutical compositions and dosage forms of the invention can further comprise one or more excipients.

Pharmaceutical compositions and dosage forms of the invention can also comprise one or more additional active ingredients. Consequently, pharmaceutical compositions and dosage forms of the invention comprise the active ingredients disclosed herein (e.g., an immunomodulatory compound of the invention, or a pharmaceutically acceptable salt, solvate, hydrate, stereoisomer, clathrate, or prodrug thereof, and an additional active ingredient). Examples of optional additional active ingredients are disclosed herein (see, e.g., section 5.2).

Single unit dosage forms of the invention are suitable for oral, mucosal (e.g., nasal, sublingual, vaginal, buccal, or rectal), or parenteral (e.g., subcutaneous, intravenous, bolus injection, intramuscular, or intraarterial), transdermal or transcutaneous administration to a patent. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise an immunomodulatory compound of the invention, or a pharmaceutically acceptable salt, solvate, hydrate, stereoisomer, clathrate, or prodrug thereof in an amount of from about 0.10 to about 150 mg. Typical dosage forms comprise an immunomodulatory compound of the invention, or a pharmaceutically acceptable salt, solvate, hydrate, stereoisomer, clathrate, or prodrug thereof in an amount of about 0.1, 1, 2, 5, 7.5, 10, 12.5, 15, 17.5, 20, 25, 50, 100, 150 or 200 mg. In a particular embodiment, a preferred dosage form comprises 4-(amino)-2-(2,6-dioxo(3-piperidyl))-isoindoline-1,3-dione (Actimid™) in an amount of about 1, 2, 5, 10, 25 or 50 mg. In a specific embodiment, a preferred dosage form comprises 3-(4-amino-1-oxo-1,3-dihydro-isoindol-2-yl)-piperidine 2,6-dione (Lenalidomide) in an amount of about 5, 10, 25 or 50 mg.

Pharmaceutical compositions may contain sufficient quantities of azacitidine to provide a daily dosage of about 10 to 150 mg/m$^2$ (based on patient body surface area) or about 0.1 to 4 mg/kg (based on patient body weight) as single or divided (2-3) daily doses. In one embodiment, dosage of azacitidine is provided via a seven day administration of 75 mg/m$^2$ subcutaneously, once every twenty-eight days, for as long as clinically necessary.

Typical dosage forms comprise the additional active ingredient in an amount of 1 to about 1000 mg, from about 5 to about 500 mg, from about 10 to about 350 mg, or from about 50 to about 200 mg. Of course, the specific amount of the additional active ingredient will depend on the specific agent used, the type of MDS being treated or managed, and the amount(s) of immunomodulatory compounds and azacitidine, and any optional additional active agents concurrently administered to the patient.

5.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, di sintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an immunomodulatory compound of the invention, anhydrous lactose, microcrystalline cellulose, polyvinylpyrrolidone, stearic acid, colloidal anhydrous silica, and gelatin.

5.4.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of an immunomodulatory compound of the invention, and its derivatives. See, e.g., U.S. Pat. No. 5,134,127, which is incorporated herein by reference.

5.4.4 Topical And Mucosal Dosage Forms

Topical and mucosal dosage forms of the invention include, but are not limited to, sprays, aerosols, solutions, emulsions, suspensions, or other forms known to one of skill in the art. See, e.g., *Remington's Pharmaceutical Sciences*, 16$^{th}$ and 18$^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, 16$^{th}$ and 18$^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5.4.5 Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of an immunomodulatory compound of the invention, or a pharmaceutically acceptable salt, solvate, hydrate, stereoisomer, prodrug, or clathrate thereof. Kits encompassed by this invention can further comprise additional active ingredients such as G-CSF, GM-CSF, EPO, topotecan, pentoxifylline, ciprofloxacin, dexamethasone, IL2, IL8, IL18, Ara-C, vinorelbine, isotretinoin, 13-cis-retinoic acid, or a pharmacologically active mutant or derivative thereof, or a combination thereof. Examples of the additional active ingredients include, but are not limited to, those disclosed herein (see, e.g., section 5.2).

Kits of the invention can further comprise devices that are used to administer the active ingredients. Examples of such devices include, but are not limited to, syringes, drip bags, patches, and inhalers.

Kits of the invention can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

6. EXAMPLES

The following studies are intended to further illustrate the invention without limiting its scope.

6.1. Clinical Studies in MDS Patients

Study 1

A Phase I trial was conducted in patients with MDS (IPSS score ≥1.5, or FAB or WHO classification with ≥5% myeloblasts). Patients were treated using below dosing schedules.

| Dose Level | Azacitidine Schedule | Lenalidomide Schedule |
| --- | --- | --- |
| 1 | 75 mg/m² SC days 1-5 | 5 mg PO days 1-14 |
| 2 | 75 mg/m² SC days 1-5 | 5 mg PO days 1-21 |
| 3 | 75 mg/m² SC days 1-5 | 10 mg PO days 1-21 |
| 4 | 50 mg/m² SC days 1-5, 8-12 | 5 mg PO days 1-14 |
| 5 | 50 mg/m² SC days 1-5, 8-12 | 5 mg PO days 1-21 |
| 6 | 50 mg/m² SC days 1-5, 8-12 | 10 mg PO days 1-21 |

Lenalidomide and Azacitidine were cyclically administered to patients with MDS. Cycling therapy involved the administration of the agents for a period of time, followed by rest for a period of time, and repeating this sequential administration. Cycles lasted 28 days, to a maximum of 7 cycles of therapy. The primary endpoint was to determine the maximum tolerated dose and dose-limiting toxicities of the combination. The secondary endpoint was response as defined by the Modified International Working Group (IWG). The combination of lenalidomide and Azacitidine was well-tolerated and the results showed efficacy in MDS patients.

Study 2

Patients receive treatment with lenalidomide at a oral dose of 5-25 mg daily on days 1 through 21, and Azacitidine at a dose of 25-75 mg/m²/d subcutaneously (SC) or intravenously (IV) on days 1 through 7 in cycles of 28 days. Patients receive treatments until disease progression or unacceptable toxicity. The combination of lenalidomide and Azacitidine is well tolerated with encouraging clinical activity. The results of this study indicate that the combination of lenalidomide and Azacitidine provides a highly effective treatment for MDS. These agents may complement each other by targeting both the bone marrow microenvironment and hypomethylating action on the malignant clone.

Study 3

Patients receive continuous treatment with lenalidomide at a oral dose of 5-25 mg daily on days 1 through 21, and Azacitidine at a oral dose of 120 mg per day on days 1 through 7 in every 28 days cycle. Patients receive treatments until disease progression or unacceptable toxicity. The results indicate that the combination dosing regimen of lenalidomide and oral Azacitidine is active and well tolerated, with a manageable side effect profile. This therapy provides a highly effective treatment for MDS.

Embodiments of the invention described herein are only a sampling of the scope of the invention. The full scope of the invention is better understood with reference to the attached claims.

What is claimed is:

1. A method of treating myelodysplastic syndromes (MDS), comprising administering to a patient in need of such treatment about 1 to about 50 mg per day of 3-(4-amino-1-oxo-1,3-didydro-isoindol-2-yl)-piperidine-2,6-dione, or a pharmaceutically acceptable salt, solvate, hydrate, stereoisomer, clathrate, or prodrug thereof and a therapeutically effective amount of cytidine analog.

2. The method of claim 1, wherein the cytidine analog is azacitidine, or a pharmaceutically acceptable salt, solvate, hydrate, or prodrug thereof.

3. The method of claim 1, wherein the symptom of the MDS includes anemia, thrombocytopenia, neutropenia, cytopenia, bicytopenia, or pancytopenia.

4. The method of claim 1, wherein the MDS is refractory anemia (RA), RA with ringed sideroblasts (RARS), RA with excess blasts (RAEB), RAEB in transformation (RAEB-T), or chronic myelomonocytic leukemia (CMML).

5. A method of improving the survival of a patient having myelodysplastic syndromes (MDS), comprising administering to the patient a therapeutically effective amount of 3 (4 amino-1-oxo-1,3-dihydro-isoindol-2-yl)-piperidine-2,6-dione, or a pharmaceutically acceptable salt, solvate, hydrate, stereoisomer, clathrate, or prodrug thereof, and a therapeutically effective amount of a cytidine analog.

6. The method of claim 5, wherein the cytidine analog is azacitidine, or a pharmaceutically acceptable salt, solvate, hydrate, or prodrug thereof.

7. The method of claim 5, wherein the MDS is refractory anemia (RA), RA with ringed sideroblasts (RARS), RA with excess blasts (RAEB), RAEB in transformation (RAEB-T), or chronic myelomonocytic leukemia (CMML).

8. A kit comprising 3 (4 amino-1-oxo-1,3-dihydro-isoindol-2-yl)-piperidine-2,6-dione, or a pharmaceutically acceptable salt, solvate, hydrate, stereoisomer, clathrate, or prodrug thereof and a cytidine analog.

9. The method of claim 1, wherein the therapeutically effective amount of the cytidine analog is about 10 to about 150 mg/m²/d.

10. The method of claim 1, wherein the therapeutically effective amount of the cytidine analog is about 10 to about 1000 mg/m²/d.

11. The method of claim 1, wherein the 3-(4-amino-1-oxo-1,3-didydro-isoindol-2-yl)-piperidine-2,6-dione is about 1 to 25 mg per day.

\* \* \* \* \*